(12) United States Patent
Head et al.

(10) Patent No.: US 6,329,372 B1
(45) Date of Patent: Dec. 11, 2001

(54) PHENYLALANINE DERIVATIVES

(75) Inventors: John Clifford Head; Sarah Catherine Archibald, both of Maidenhead; Graham John Warrellow, Northwood; John Robert Porter, Chinnor, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/237,060

(22) Filed: Jan. 26, 1999

(30) Foreign Application Priority Data

Jan. 27, 1998 (GB) .................................................. 9801674
Dec. 3, 1998 (GB) .................................................. 9826669

(51) Int. Cl.$^7$ ........................... A01N 43/64; A01N 43/80; A61K 31/53; C07D 251/00; C07D 237/26; C07D 333/56; C07D 307/78; C07C 205/00

(52) U.S. Cl. .................... 514/241; 514/242; 514/255.06; 514/256; 514/259; 514/300; 514/303; 514/307; 514/311; 514/343; 514/354; 514/355; 514/356; 514/361; 514/362; 514/363; 514/364; 514/367; 514/371; 514/372; 514/374; 514/378; 514/383; 514/399; 514/406; 514/419; 514/423; 544/180; 544/182; 544/234; 544/335; 544/406; 548/308.5; 549/57; 549/79; 549/467; 549/487; 560/21; 560/22

(58) Field of Search ........................ 560/11, 22; 514/343, 514/242, 241, 255.06, 259, 256, 300, 303, 307, 311, 354, 355, 356, 361, 362, 363, 364, 367, 371, 372, 374, 378, 383, 399, 406, 419, 423; 546/279.1, 123, 113, 146, 169, 262; 544/182, 180, 224, 335, 406; 548/125, 131, 143, 136, 248, 236, 200, 214, 178, 179, 217, 260, 255, 266.8, 333.5, 374.1, 537, 538, 304.4, 304.5, 253; 549/57, 79, 467, 487

(56) References Cited

U.S. PATENT DOCUMENTS

| | | | |
|---|---|---|---|
| 4,101,661 | * 7/1978 | Kaltenbronn | 424/266 |
| 4,470,973 | 9/1984 | Natarajan et al. | 424/177 |
| 4,554,273 | 11/1985 | Bayssat et al. | 514/221 |
| 4,987,132 | 1/1991 | Mase et al. | 514/252 |
| 5,164,372 | 11/1992 | Matsuo et al. | 514/19 |
| 5,227,490 | 7/1993 | Hartman et al. | 514/317 |
| 5,260,277 | 11/1993 | McKenzie | 544/18 |
| 5,296,486 | 3/1994 | Lazer et al. | 514/333 |
| 5,510,346 | 4/1996 | Martin et al. | 514/221 |
| 5,698,691 | 12/1997 | Yukimasa et al. | 540/490 |
| 5,773,646 | 6/1998 | Michael et al. | 562/439 |
| 6,093,696 | 7/2000 | Head et al. | 514/19 |
| 6,229,011 | * 5/2001 | Chen et al. | 544/171 |

FOREIGN PATENT DOCUMENTS

| | | |
|---|---|---|
| 23 16 881 A | 10/1973 | (DE) . |
| 28 37 264 A1 | 3/1979 | (DE) . |
| 196 54 483 A | 1/1998 | (DE) . |
| 0 031 104 A1 | 7/1981 | (EP) . |
| 0 048 763 A1 | 4/1982 | (EP) . |
| 0 144 230 A | 6/1985 | (EP) . |
| 0 288 176 A | 10/1988 | (EP) . |
| 0 322 068 A1 | 6/1989 | (EP) . |
| 0307837 | * 11/1989 | (EP) . |
| 0 394 989 A2 | 10/1990 | (EP) . |
| 0 498 268 A2 | 8/1992 | (EP) . |
| 0 596 406 A1 | 5/1994 | (EP) . |
| 0 710 657 A1 | 5/1996 | (EP) . |
| 0 710 659 A1 | 5/1996 | (EP) . |
| 0 842 943 A2 | 5/1998 | (EP) . |
| 0 842 945 A2 | 5/1998 | (EP) . |
| 56005483 | * 1/1981 | (JP) . |
| 56 090045 | 7/1981 | (JP) . |
| 03 135962 | 6/1991 | (JP) . |
| WO 86/02353 | 4/1986 | (WO) . |
| WO 93/00095 | 1/1993 | (WO) . |
| WO 93/08174 | 4/1993 | (WO) . |
| WO 93/09795 | 5/1993 | (WO) . |
| WO 94/15954 | 7/1994 | (WO) . |
| WO 94/15955 | 7/1994 | (WO) . |
| WO 94/29285 | 12/1994 | (WO) . |
| WO 95/13811 | 5/1995 | (WO) . |

(List continued on next page.)

OTHER PUBLICATIONS

Lobb, R.R., et al., "Small molecule antagonists of a alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

(List continued on next page.)

*Primary Examiner*—Mukund J. Shah
*Assistant Examiner*—Tamthom N. Truong
(74) *Attorney, Agent, or Firm*—Woodcock Washburn Kurtz Mackiewicz & Norris LLP

(57) ABSTRACT

Phenylalanine derivatives of formula (1) are described:

$$R^1(Alk^1)_r(L^1)_s \underset{R^b}{\overset{R^a}{\text{—Ar—}}} (Alk^2)_m\text{—}\underset{R}{\overset{}{C}}(R^2)\text{—}N(R^3)COHet \quad (1)$$

wherein
  R is a carboxylic acid or a derivative thereof;
  $L^1$ is a linker atom or group;
  Het is an optionally substituted heteroaromatic group;
and the salts, solvates, hydrates and N-oxides thereof.

The compounds are able to inhibit the binding of alpha4 integrins to their ligands and are of use in the prophylaxis and treatment of immune or inflammatory disorders.

19 Claims, No Drawings

FOREIGN PATENT DOCUMENTS

| | | |
|---|---|---|
| WO 95/15973 | 6/1995 | (WO) . |
| WO 95/19356 | 7/1995 | (WO) . |
| WO 95/35314 | 12/1995 | (WO) . |
| WO 96/01644 | 1/1996 | (WO) . |
| WO 96/22966 | 8/1996 | (WO) . |
| WO 96/26190 | 8/1996 | (WO) . |
| WO 97/03094 | 1/1997 | (WO) . |
| WO 97/08145 | 3/1997 | (WO) . |
| WO 97/12866 | 4/1997 | (WO) . |
| WO 97/31907 | 9/1997 | (WO) . |
| WO 97/36859 | 10/1997 | (WO) . |
| WO 98/00395 | 1/1998 | (WO) . |
| WO 98/04247 | 2/1998 | (WO) . |
| WO 98/04913 | 2/1998 | (WO) . |
| WO 98/42662 | 10/1998 | (WO) . |
| WO 98/53814 | 12/1998 | (WO) . |
| WO 98/53817 | 12/1998 | (WO) . |
| WO 98/53818 | 12/1998 | (WO) . |
| WO 98/54207 | 12/1998 | (WO) . |
| WO 98/58902 | 12/1998 | (WO) . |
| WO 99/06390 | 2/1999 | (WO) . |
| WO 99/06431 | 2/1999 | (WO) . |
| WO 99/06432 | 2/1999 | (WO) . |
| WO 99/06433 | 2/1999 | (WO) . |
| WO 99/06434 | 2/1999 | (WO) . |
| WO 99/06435 | 2/1999 | (WO) . |
| WO 99/06436 | 2/1999 | (WO) . |
| WO 99/06437 | 2/1999 | (WO) . |
| WO 99/10312 | 3/1999 | (WO) . |
| WO 99/10313 | 3/1999 | (WO) . |
| WO 99/20272 | 4/1999 | (WO) . |
| WO 99/30709 | 6/1999 | (WO) . |
| WO 99/35163 | 7/1999 | (WO) . |
| WO 99/37618 | 7/1999 | (WO) . |
| WO 99/43642 | 9/1999 | (WO) . |
| WO 99/48879 | 9/1999 | (WO) . |
| WO 99/61465 | 12/1999 | (WO) . |
| WO 00/35855 | 6/2000 | (WO) . |

OTHER PUBLICATIONS

Ŝavrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Frank, R., et al., "Extremely mild reagent for Boc deprotection," *J. Chem. Commun. (Cambridge)*, 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. no. 83:97276 (abstract only, 5 pages).

Masuda, T., *Jpn. Kodai Tokkyo Koho*, 22 pages, doc. No. 115:280022 (abstract only, 1 page), 1991.

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (asbtract only, 2 pages), 1991.

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages), 1983.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Abraham, W.M. et al., "$\alpha_4$–Integrins Mediate Antigen–Induced Late Bronchial Responses and Prolonged Airway Hyperresponsiveness in Sheep", *J. Clin. Invest.*, 1994, 93, 776–787.

Berlin, C. et al., "$\alpha 4\beta 7$ Integrin Mediates Lymphocyte Binding to the Mucosal Vascular Addressin MAdCAM–1", *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", *J. Immunol.*, 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule", *J. Biol. Chem.*, 1994, 269(28), 18668–18673.

Ferguson, T.A. et al., "Two integrin–binding peptides abrogate T cell–mediated immune responses in vivo", *Proc. Natl. Acad. Sci. USA*, 1991, 88, 8072–8076.

Holzmann, B. et al., "Peyer's patch–specific lymphocyte homing receptors consist of a VLA–4–like α chain associated with either of two integrin β chains, one of which is novel", *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design", *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.*, 1992, 149(10), 3394–3402.

Li, Z. et al., "Effect of an anti–Mo1 MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Osborn, L. et al., "Direct Expression Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–α4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of $\alpha 4$ Integrins", *J. Immunol.*, 1997, 158, 1710–1718.

Yang, X., "A predominant role of integrin $\alpha 4$ in the spontaneous developments of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies agains $\alpha 4\beta 1$ integrin", *Nature*, 1992, 356, 63–66.

WPI/ Derwent No. XP–002076854, Japanese Patent No. JP 04 193 895 A (Ajinomoto, K.K.), Jul. 13, 1992, DW9234, 1 Page, Abstract Only.

WPI/ Derwent No. XP–002076855, Japanese Patent No. JP 56 049 373 A (Dainippon Pharm Co Ltd), May 2, 1981, DW8125, 1 Page, Abstract Only.

Corey, E.J. et al., "A Synthetic Method for Formyl $\rightarrow$ Ethynyl Conversion (RCHO $\rightarrow$ RC$\equiv$CH or RC$\equiv$CR')", *Tetrahedron Lett.*, 1972, 36, 3769–3772.

Lei, H. et al., "Efficient Synthesis of a Phosphinate Bis–Amino Acid and Its Use in the Construction of Amphiphilic Peptides", *J. Org. Chem.*, 1994, 59, 4206–4210.

Nagasawa, H.T. et al., "$\alpha$–Substituted Cysteines as Sequestering Agents for Ethanol–Derived Acetaldehyde in Vivo", *J. Med. Chem.*, 1987, 30, 1373–1378.

Osborne, L., "Leukocyte Adhesion to Endothelium in Inflammation", *Cell*, 1990, 62, 3–6.

Suh et al. (Bioorg. Med. Chem. Lett. 5(6), pp. 585–588, (1995).*

Abstract of El–Naggar et al. (Farmaco, Ed. Sci. 40(9), pp. 662–670). See the abstract (CA 103:175277), (1985).*

Abstract of El–Naggar et al. (Farmaco, Ed. Sci. 40(10), pp. 786–794). See the abstract (CA 104:130251), (1985).*

Bach et al., "Anomalous optical rotation and circular dichroism of N–thioacylated.alpha–amino acids and deriva," *Acta Chem. Scand.*, 1966, 20(10), 2781–2794.

Barrett, G.C., "Circular dichroism of N–thiobenzoly–1–$\alpha$–amino acids. III. Their circular dichroism through the near–ultraviolet wavelength range," *J. Chem. Soc.*, 1967, Section C, 1–5.

*Chemical Abstracts*, "N–[4–Thiazolidinyl)carbonyl]amino acid derivatives," 1981, 95(19), Abstract No. 169173f, 1 page.

Cornforth, J.W., "Oxazoles and Oxazolones," *Chem. Penicillin*, Princeton Book Review, 1949, pp. 688, 799, and 800.

Fu, H. et al., "Preliminary study on synthesis and antitumor activity in vitro of derivatives of timonacic," *Chemicals Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of $\alpha$–amino dithioesters and endothiodipeptides," *J. Prakt. Chem.*, 1996, 338(3), 251–256.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of $\alpha$–Thioacylamino–acids. Their conversion into Thiazolones and Derivatives Thereof," *J. Chem. Soc.*, 1955, 1791–1797.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Schultz, Von O.–E. et al., "Analogos of nuleic acid based as antimetabolites," *Arzneimittel Forschung. Drug Res.*, 1967, 17(8), 1060–1064 (English summary included).

Tsunematsu, H. et al., "Hydrolysis of phenylthiazolones of p–guanidinophenylalanine and arginine by trypsin and related enzymes," *J. Biochem.*, 1983, 94(4), 1119–1125.

Whitlock, B.J. et al., "Structure and synthesis of lathyrine," *J. Org. Chem.*, 1965, 30, 115–118.

Buckle, D.R., et al., "Non Thiazolidinedione Antihyperglycaemic Agents. 1: $\alpha$–Heteroatom Substituted $\beta$–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (av$\beta_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazpinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 114926r, 1 page.

* cited by examiner

PHENYLALANINE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus, the integrin termed α4β1 consists of the integrin alpha 4 associated with the integrin beta 1 chain, but is also widely referred to as Very Late Antigen 4 VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3 (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4 β1, binds to VCAM-1 and fibronectin. In addition, α4β7 binds to an adhesion molecule believed to be involved in the homing of leukocytes to mucosal tissue termed MAdCAM-1 [Berlin, C. et al. Cell, 74, 185, (1993)]. The interaction between α4β7 ad MAdCAM-1 may also be important at sites of inflammation outside of mucosal tissue [Yang, X-D. et al. PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al. PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family is it very important to be able to identify selective inhibitors of the alpha 4 subgroup.

We have now found a group of compounds which are potent and selective inhibitors of α4 integrins. Members of the group are able to inhibit α4 integrins such as α4β1 and /or α4β7 at concentrations at which they generally have no or minimal inhibitory action on α integrins of other subgroups. The compounds are thus of use in medicine, for example in the prophylaxis and treatment of immune or inflammatory disorders as described hereinafter.

Thus according to one aspect of the invention we provide a compound of formula (1)

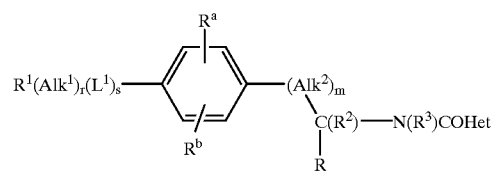

(1)

wherein

R is a carboxylic acid or a derivative thereof;

$R^1$ is a hydrogen atom or a hydroxyl, straight or branched alkoxy or optionally substituted cycloaliphatic, polycycloaliphatic, heterocycloaliphatic, polyheterocycloaliphatic, aromatic or heteroaromatic group;

$Alk^1$ is an optionally substituted aliphatic or heteroaliphatic chain;

$L^1$ is a linker atom or group;

r and s, which may be the same or different, is each zero or an integer 1 provided that when r is zero $R^1$ is an optionally substituted cycloaliphatic, polycycloaliphatic, heterocycloaliphatic, polyheterocycloaliphatic, aromatic or heteroaromatic group;

$R^a$ and $R^b$, which may be the same or different is each an atom or group —$L^2(CH_2)_pL^3(R^c)_q$ in which $L^2$ and $L^3$ is each a covalent bond or a linker atom or group, p is zero or the integer 1, q is an integer 1, 2 or 3 and $R^c$ is a hydrogen or halogen atom or a group selected from straight or branched alkyl, —$OR^d$ [where $R^d$ is a hydrogen atom or an optionally substituted straight or branched alkyl group], —$SR^d$, —$NR^dR^e$, [where $R^e$ is as just defined for $R^d$ and may be the same or different], —$NO_2$, —CN, —$CO_2R^d$, —$SO_3H$, —$SO_2R^d$, —$OCO_2R^d$, —$CONR^dR^e$, —$OCONR^dR^e$, —$CSNR^dR^e$, —$COR^d$, —$N(R^d)COR^e$, $N(R^d)CSR^e$, —$SO_2N(R^d)(R^e)$, —$N(R^d)SO_2R^e$, —$N(R^d)CONR^eR^f$ [where $R^f$ is a hydrogen atom or an optionally substituted straight or branched alkyl group], —$N(R^d)CSNR^eR^f$ or —$N(R^d)SO_2NR^eR^f$;

$Alk^2$ is a straight or branched alkylene chain;

m is zero or an integer 1;

$R^2$ is a hydrogen atom or a methyl group;

$R^3$ is a hydrogen atom or a straight or branched alkyl group;

Het is an optionally substituted heteroaromatic group; and the salts, solvates, hydrates and N-oxides thereof. it will be appreciated that compounds of formula (1) may have one or more chiral centres. Where one or more chiral centres is present, enantiomers or diastereomers may exist, and the invention is to be understood to extend to all such enantiomers, diasteromers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular estes and amides include —$CO_2Alk^4$ and —$CON(R^4)_2$ groups as described herein.

When in the compounds of the invention $L^1$ is present as a linker atom or group it may be any divalent linking atom or group. Particular examples include —O— or —S— atoms or —C(O)—, —C(O)O—, —C(S)—, —S(O)—, —$S(O)_2$—, —$N(R^4)$— [where $R^4$ is a hydrogen atom or a straight or branched alkyl group], —$CON(R^4)$—, —OC(O)$N(R^4)$—, —$CSN(R^4)$—, —$N(R^4)CO$—, —$N(R^4)C(O)O$—, —$N(R^4)CS$—, —$S(O)N(R^4)$—, —$S(O)_2N(R^4)$—, —$N(R^4)S(O)$—, —$N(R^4)S(O)_2$—, —$N(R^4)CON(R^4)$—, —$N(R^4)CSN(R^4)$—, —$N(R^4)SON(R^4)$— or —$N(R^4)SO_2N(R^4)$— groups. Where the linker group contains two $R^4$ substituents, these may be the same or different.

$Alk^2$ in the compounds of the invention may be for example a straight or branched $C_{1-3}$alkylene chain. Particular examples include —$CH_2$—, —$CH(CH_3)$—, —$C(CH_3)_2$— and —$(CH_2)_2$—.

When $R^3$ and/or $R^4$ in the compounds of formula (1) is a straight or branched alkyl group it may be a straight or branched $C_{1-6}$alkyl group, e.g. a $C_{1-6}$alkyl group such as a methyl or ethyl group.

When $Alk^1$ in compounds of formula (1) is an optionally substituted aliphatic chain it may be an optionally substituted $C_{1-10}$ aliphatic chain. Particular examples include optionally substituted straight or branched chain $C_{1-6}$ alkyl, $C_{2-6}$ alkenyl, or $C_{2-6}$ alkynyl chains.

Heteroaliphatic chains represented by $Alk^1$ include the aliphatic chains just described but with each chain additionally containing one, two, three or four heteroatoms or heteroatom-containing groups. Particular heteroatoms or groups include atoms or groups $L^4$ where $L^4$ is as defined above for $L^1$ when $L^1$ is a linker atom or group. Each $L^4$ atom or group may interrupt the aliphatic chain, or may be positioned at its terminal carbon atom to connect the chain to the above or group $R^1$.

Particular examples of aliphatic chains represented by $Alk^1$ include optionally substituted —$CH_2$, —$CH_2CH_2$—, —$CH(CH_3)$—, —$C(CH_3)_2$—, —$(CH_2)_2CH_2$—, —$CH(CH_3)CH_2$—, —$CH(CH_2)_3CH_2$—, —$CH(CH_3)CH_2CH_2$—, —$CH_2CH(CH_3)CH_2$—, —$C(CH_3)_2CH_2$—, —$(CH_2)_4CH_2$—, —$(CH_2)_5CH_2$—,—CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one ore two atoms and/or groups $L^4$ to form an optionally substituted heteroaliphatic chain. Particular examples include optionally substituted —$L^4CH_2$—, —$CH_2L^4CH_2$—, —$L^4(CH_2)_2$—, —$CH_2L^4(CH_2)_2$—, —$(CH_2)_2L^4CH_2$—, —$L^4(CH_2)_3$— and —$(CH_2)_2L^4(CH_2)_2$— chains. The optional substituents which may be present on aliphatic or heteroaliphatic chains represented by $Alk^1$ include one, two, three or more substituents selected from halogen atoms, e.g. fluorine, chlorine, bromine or iodine atoms, or hydroxyl, $C_{1-6}$alkoxy, e.tg. methoxy or ethoxy, thiol, $C_{1-6}$alkylthio e.g. methylthio or ethylthio, amino or substituted amino groupss. Substituted amino groups include —$NHR^4$ and —$N(R^4)_2$ groups where $R^4$ is a straight or branched alkyl group as defined above. Where two $R^4$ groups are present these may be the same or different. Particular examples of substituted chains represented by $Alk^1$ include those specific chains just described substituted by one, two, or three halogen atoms such as fluorine atoms, for example chains of the type —$CH(CF_3)$—, —$C(CF_3)_2$— —$CH_2CH(CF_3)$—, —$CH_2C(CF_3)_2$—, —$CH(CF_3)$— and —$C(CF_3)_2CH_2$.

Alkoxy groups represented by $R^1$ in compounds of the invention include straight of branched $C_{1-6}$alkoxy groups such as methoxy and ethoxy groups.

When $R^1$ is present in compounds of formula (1) as an optionally substituted cycloaliphatic group it may be an optionally substituted $C_{3-10}$cycloaliphatic group. Particular examples include optionally substituted $C_{3-10}$cycloalkyl, e.g. $C_{3-7}$cycloalkyl, $C_{3-10}$cycloalkenyl e.g. $C_{3-7}$cycloalkenyl or $C_{3-10}$cycloalkynyl e.g. $C_{3-7}$cycloalkynyl groups.

Optionally substituted heterocycloaliphatic groups represented by $R^1$ include the optionally substituted cycloaliphatic groups just described for $R^1$ but with each group additionally containing one, two, three or four heteroatoms or heteroatom-containing groups $L^2$ as just defined.

Optionally substituted polycycloaliphatic groups represented by $R^1$ include optionally substituted $C_{7-10}$ bi- or tricycloalkyl or $C_{7-10}$bi- or tricycloalkenyl groups. Optionally substituted polyheterocycloaliphatic groups represented by $R^1$ include the optionally substituted polycycloalkyl groups just described, but with each group additionally containing one, two, three or four $L^2$ atoms or groups.

Particular examples of $R^1$ cycloaliphatic, polycycloaliphatic, heterocycloaliphatic and polyheterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3- , 6H-1,3-, 6H-1,2-, 2H-1,2- or 4H-1,4-oxazinyl, isoxazinyl, oxathiazinyl, e.g. 1,2,5 or 1,2,6-oxathiazinyl, or 1,3,5-oxadiazinyl groups.

The optional substituents which may be present on the $R^1$ cycloaliphatic, polycycloaliphatic, heterocycloaliphatic or polyheterocycloaliphatic groups include one, two, three or more substituents represented by $R^5$ in which $R^5$ is selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, hydroxyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, —N($R^4$)$_2$, —CN, —CO$_2$$R^4$, —NO$_2$, —CON($R^4$)$_2$, —CSN($R^4$)$_2$, —COR$^4$, —CSN($R^4$)$_2$, —N($R^4$)COR$^4$, —N($R^4$)CSR$^4$, —SO$_2$N($R^4$)$_2$, —N($R^4$)SO$_2$$R^4$, —N($R^4$)CON($R^4$)$_2$, —N($R^4$)CSN($R^4$) and —N($R^4$)SO$_2$N($R^4$)$_2$ groups. In these substituents the group $R^4$ when present is a hydrogen atom or a straight or branched alkyl group as defined above. When more than one $R^4$ group is present in a substituent each group may be the same or different. The substituent may be present on any available carbon atom or where appropriate any nitrogen atom, in the $R^1$ group.

In the compounds of formula (1), optionally substituted aromatic groups represented by the group $R^1$ include for example monocyclic or bicyclic fused ring $C_{6-12}$ aromatic groups, such as phenyl, 1- or 2- naphthyl, 1- or 2-tetrahydronaphthyl, indanyl or indenyl groups, optionally substituted by one, two, three or more —L$^2$(CH$_2$)$_p$L$^3$(R$^c$)$_q$ atoms or groups, where $L^2$, $L^3$, p and q are as previously defined and $R^c$ is as previously defined but is other than a hydrogen atom when $L^2$ and $L^3$ is each a covalent bond and p is zero.

Optionally substituted heteroaromatic groups, represented by the group $R^1$ or Het in compounds of formula (1) include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N-$C_{1-6}$aimidazolyl, oxazolyl, isoxazoly, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro] benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro] benzopyranyl, quinazolinyl, naphthyridinyl, pyrido[3,4-b] pyridyl pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on $R^1$ heteroaromatic groups include one, two, three or more —L$^2$ (CH$_2$)$_p$L$^3$(R$^c$)$_q$ atoms on groups as just defined.

Examples of the substituents represented by $R^a$ and $R^b$ in compounds of formula (1) and which may be present on aromatic or heteroaromatic groups represented by $R^1$ include atoms or groups —L$^2$(CH$_2$)$_p$LR$^c$, —L$^2$(CH$_2$)$_p$R$^c$, —L$^2$R$^c$, —(CH$_2$)$_p$R$^c$ and —R$^c$ wherein $L^2$, (CH$_2$)$_p$, L and $R^c$ are as defined above. Particular examples of such substituents include —L$^2$CH$_2$L$^2$R$^c$, —L$^2$CH(CH$_3$)L$^3$R$^c$, —L$^2$(CH$_2$)$_2$L$^3$R$^c$, —2CH$_2$R$^c$, —L$^2$CH(CH$_3$)R$^c$, —L$^2$(CH$_2$)$_2$R$^c$, —CH$_2$R$^c$, —CH(CH$_3$)R$^c$ and —(CH$_2$)$_2$R$^c$ groups.

Thus each of $R^a$ and $R^b$ and, where present, substituents on $R^1$ aromatic or heteroaromatic groups in compounds of the invention may be for example selected from a hydrogen atom, a halogen atom, e.g. a fluorine, chlorine, bromine or iodine atom, or $C_{1-6}$alkyl, e.g. methyl, ethyl, n-propyl, i-propyl, n-butyl or t-butyl, $C_{1-6}$alkylamino, e.g. methylamino or ethylamino, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$, —CHF$_2$, CH$_2$F, halo$C_{1-6}$alkoxy, e.g. —OCF$_3$, —OCHF$_2$, —OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$alkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, nitro, cyano, amidino, hydroxyl (—OH), formyl [HC(O)—], carboxyl (—CO$_2$H), —CO$_2$R$^{12}$, $C_{1-6}$ alkanoyl e.g. acetyl, thiol (—SH), thio$C_{1-6}$alkyl, e.g. thiomethyl or thioethyl, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$alkylaminocarbonyl, e.g. methylaminocarbonyl or ethylaminocarbonyl, $C_{1-6}$alkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylamionocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$-dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonyl-amino or diethylsulphonylamino, aminosulphonylamino ($-NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimmethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino group.

Optional substituents present on the heteroaromatic groups represented by Het include one, two, three or more substituents, each selected from an atom or group $R^6$ in which $R^6$ is $-R^{6a}$ or $-Alk^3(R^{6a})_m$, where $R^{6a}$ is a halogen atom, or an amino ($-NH_2$), substituted amino, nitro, cyano, amidino, hydroxyl ($-OH$) substituted hydroxyl, formyl, carboxyl ($-CO_2H$). esterified carboxyl, thiol ($-SH$), substituted thiol, $-COR^7$ [where $R^7$ is an $-Alk^3(R^{6a})_m$, aryl or heteroaryl group], $-CSR^7$, $-SO_3H$, $-SO_2R^7$ $-SO_2NH_2$, $-SO_2NHR^7$ $SO_2N(R^7)_2$, $-CONH_2$, $-CSNH_2$, $-CONHR^7$, $-CSNHR^7$, $-CON[R^7]_2$, $-CSN(R^7)_2$, $-N(R^4)SO_2R^7$, $-N(SO_2R^7)_2$, $-NH(R^4)SO_2NH_2$, $-N(R^4)SO_2NHR^7$, $-N(R^4)SO_2N(R^7)_2$, $-N(R^4)COR^7$, $-N(R^4)CON(R^7)_2$, $-N(R^4)CSN(R^7)_2$, $-N(R^4)CSR^7$, $-N(R^4)C(O)OR^7$, $-SO_2NHet^1$ [where $-NHet^1$ is an optionally substituted $C_{5-7}$cyclicamino group optionally containing one or more other $-O-$ or $-S-$ atoms or $-N(R^4)-$, $-C(O)-$ or $-C(S)-$ groups ], $-CONHet^1$, $-CSNHet^1$, $-N(R^4)SO_2NHet^1$, $-N(R^4)CONHet^1$, $-N(R^4)CSNHet^1$, $-SO_2N(R^4)Het^2$ [where $Het^2$ is an optionally substituted monocyclic $C_{5-7}$carbocyclic group optionally containing one or more $-O-$ or $-S-$ atoms or $-N(R^4)-$, $-C(O)-$ or $-C(S)-$ groups], $-CON(R^4)Het^2$, $-CSN(R^4)Het^2$, $-N(R^4)CON(R^4)Het^2$, $-N(R^4)CSN(R^4)Het^2$, aryl or heteroaryl group; $Alk^3$ is a straight or branched $C_{1-6}$alkylene, $C_{2-6}$alkenylene or $C_{2-6}$alkynylene chain, optionally interrupted by one, two or three $-O-$ or $-S-$ atoms or $-S(O)_n$ [where n is an integer 1 or 2] or $-N(R^8)-$ groups [where $R^8$ is a hydrogen atom or $C_{1-6}$alkyl, e.g. methyl or ethyl group]; and m is zero or an integer 1, 2 or 3. It will be appreciated that when two $R^4$ or $R^7$ groups are present in one or the above substituents, the $R^4$ or $R^7$ groups may be the same or different.

When in the group $-Alk^3(R^{6a})_m$ is an integer 1, 2 or 3, it is to be understood that the substituent or substituents $R^{6a}$ may be present or any suitable carbon atom in $-Alk^3$. Where more than one $R^{6a}$ substituent is present these may be the same or different and may be present on the same or different atom in $-Alk^3$. Clearly, when m is zero and no substituent $R^{6a}$ is present the alkylene, alkenylene or alkynylene chain represented by $Alk^3$ becomes an alkyl, alkenyl or alkynyl group.

When $R^{6a}$ is a substituted amino group it may be for example a group $-NHR^7$ [where $R^7$ is as defined above] or a group $-N(R^7)_2$ wherein each $R^7$ group is the same or different.

When $R^{6a}$ is a halogen atom it may be for example a fluorine, chlorine, bromine, or iodine atom.

When $R^{6a}$ is a substituted hydroxyl or substituted thiol group it may be for example a group $-OR^7$ or a $-SR^7$ or $-SC(=NH)NH_2$ group respectively.

Esterified carboxyl groups represented by the group $R^{6a}$ include groups of formula $-CO_2Alk^4$ wherein $Alk^4$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^4$ group include $R^{6a}$ substituents described above.

When $Alk^3$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three $-O-$ or $-S-$, atoms or $-S(O)-$, $-S(O)_2-$ or $-N(R^8)-$ groups.

Aryl or heteroaryl groups represented by the groups $R^{6a}$ or $R^7$ include mono- or bicyclic optionally substituted $C_{6-12}$ aromatic or $C_{1-9}$ heteroaromatic groups as described above for the groups $R^1$ and Het.

The aromatic and heteroaromatic groups may be attached to the remainder of the compound of formula (1) by any carbon or hetero e.g. nitrogen atom as appropriate.

When $-NHet^1$ or -$Het^2$ forms part of a substituent $R^6$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on $-NHet^1$ or -$Het^2$ include those $R^5$ substituents described above.

Particularly useful atoms or groups represented by $R^6$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrrolyl, furyl, thiazolyl, or thienyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $c_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyloxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^4$ [where $Alk^4$ is as defined above], $C_{1-6}$ alkanoyl e.g. acetyl, optionally substituted benzoyl, thiol (—SH), thio$C_{1-6}$alkyl, e.g. thiomethyl or thioethyl, —SC(=NH)$NH_2$, sulphonyl (—$SO_3H$), $C_{1-6}$alkylsulphonyl, e.g. methylsulphonyl, optionally substituted phenylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylamino-sulphonyl, carboxamido (—$CONH_2$), $C_{1-6}$alkylaminocarbonyl, e.g. methylalkylaminocarbonyl or ethylalkylaminocarbonyl, $C_{1-6}$dialkylalkylaminocarbonyl, e.g. dimethylalkylaminocarbonyl or diethylalkylaminocarbonyl, amino$C_{1-6}$alkylaminocarbonyl, e.g. aminoethylalkylaminocarbonyl, $C_{1-6}$alkylamino$C_{1-6}$alkylalkylaminocarbonyl, e.g. diethylaminoethylalkylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocarbonyl$C_{1-6}$alkylamino, e.g. methylaminocarbonylmethylamino, aminothiocarbonylamino, $C_{1-6}$alkylthiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonyl-amino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoyl-amino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, benzylthio, pyridylmethylthio or thaizolylmethylthio groups.

In the above groups of particularly useful $R^6$ substituents, the reference to optional substitution is intended to relate primarily to the aromatic or heteroaromatic portions of the groups described. Thus for example such groups may be optionally mono-, di- or tri-substituted by those particular atoms or groups described above for each of $R^a$ and $R^b$.

Where desired, two $R^6$ substituents may be linked together to form a cyclic group such as a cyclic ether, e.g. a $C_{1-6}$alkylenedioxy group such as methylenedioxy or ethylenedioxy.

It will be appreciated that where two or more $R^6$ substituents are present, these need not necessarily be the same atoms and/or groups. In general, the substituent(s) may be present at any available ring position in the heteroaromatic group represented by Het.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

R in compounds of the invention is preferably a —$CO_2H$ group.

When present, the aliphatic chain represented by $Alk^1$ in compounds of the invention is preferably a —$CH_2$— chain.

$Alk^2$ in compounds of formula (1) is preferably a —$CH_2$— chain and m is preferably an integer 1. In compounds of this type, the carbon atom to which $Alk^2$ and R are attached forms a chiral centre and is preferably in the L configuration.

$R^2$ in compounds of formula (1) is preferably a hydrogen atom.

$R^3$ in compounds of the invention is preferably a hydrogen atom.

In general in compounds of the invention —$(Alk^1)_r(L^1)_s$ is preferably —$CH_2O$—, —$SO_2NH$—, —C(O)O— or —CON($R^4$)— and is especially —CONH—.

In general in compounds of the invention the group $R^1$ is preferably an optionally substituted aromatic or heteroaromatic group. Particularly useful groups of these types include optionally substituted phenyl, pyridyl or pyrimidinyl groups, particularly those in which the substituent when present is an atom or group —$L^2(CH_2)_pL^3(R^c)_q$ as described above. Each substituent may be present on any available ring carbon or nitrogen atom.

The heteroaromatic group represented by Het in compounds of formula (1) is preferably on optionally substituted $C_{3-5}$ monocyclic heteroaromatic group containing one, two or three heteroatoms selected from oxygen, sulphur or nitrogen atoms. Particularly useful groups of this type include optionally substituted pyrrolyl and pyridyl groups. Especially useful heteroaromatic groups represented by Het include optionally substituted 3- or 4-pyridyl groups, particularly 2-monosubstituted 3- or 4-pyridyl or 2,6-disubstituted 3- or 4-pyridyl groups. In these, and in general in the group Het, the optional substituent when present is preferably an atom or group $R^6$ as defined above.

A particularly useful class of compounds according to the invention has the formula (1a)

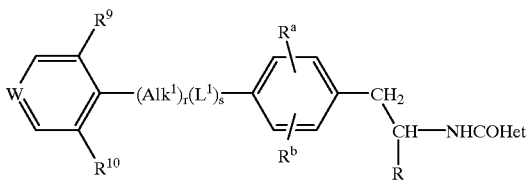

(1a)

wherein —W= is —CH= or —N=, $R^9$ and $R^{10}$, which may be the same or different is each a —$L^2(CH_2)_pL^3(R^c)_q$ atom or group as generally and particularly defined above, and $Alk^1$, r, $L^1$, s, $R^a$, $R^b$, R and Het are as generally and particularly defined above, and the salts, solvates, hydrates and N-oxides thereof.

It will be appreciated that the various preferences stated above in relation to groups present in compounds of formula (1) apply equally to the same groups when present in compounds of formula (1).

Additionally, in the compounds of formula (1a) -$(Alk^1)_r$-$(L^1)_s$— is preferably a —$CH_2O$ or —$CON(R^4)$— group and is especially a —CONH— group. Het is preferably an optionally substituted pyrrolyl or especially an optionally substituted pyridyl group.

Particularly useful compounds of formula (1a) are those wherein Het is a 2-monosubstituted 3- or 4-pyridyl group or a 2,6-disubstituted 3- or 4-pyridyl group.

One of $R^9$ or $R^{10}$ in compounds of formula (1a) may be for example a hydrogen atom and the other a substituent $L^2(CH_2)_pL^3(R^c)_q$ in which $R^c$ is not a covalent bond and p is zero, but preferably each of $R^9$ and $R^{10}$ is a substituent —$L(^2CH_2)_pL^3(R^c)_q$ where $R^3$ is as just defined. Particularly useful $R^9$ or $R^{10}$ substituents include a hydrogen atom or a halogen atom, especially fluorine or chlorine atoms, or a methyl, ethyl, methoxy, ethoxy, —$CF_3$, —OH, —CN, —$NO_2$, —$NH_2$, —$NHCH_2$, —$N(CH_3)_2$, —$COCH_3$, —$SCH_3$, —$CO_2H$ or —$CO_2CH_3$ group.

Particularly useful compounds according to the invention include the following:

2-Thio(S-2,5-dimethoxyphenyl)nicotinoyl-(N-2,6-dichlorobenzoyl)-L-4-aminophenylalanine;

2-Thio(S-2,5-dimethoxyphenyl)nicotinoyl-(N-2,6-dichlorobenzoyl)-L-4-aminophenylalanine;

N-(3,5-Dichloro-4-picolyl)-N'-(3,5-dichloro-4-picolyl)-L-4-aminophenylalanine;

N-(2-Chloronicotinoyl)-N'-(3,5-dichloro-4-picolyl)-L-4-amino-phenylalanine;

O-(2,6-dichlorobenzyl)-N-(4-acetyl-1,2,5-trimethyl-3-pyrroyl)-L-tyrosine;

(N'-3,5-Dichloroisonicotinoyl)-N-{([3-pyridinylmethyl]thio)isonicotinoyl}-L-4-aminophenylalanine;

N-(4-Acetyl-1,2,5-trimethyl-1H-pyrrole-3-carbonyl)-N'-(3,5-dichloro-4-picolyl)-L-4-aminophenylalanine; and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter. In particular compounds of the invention, such as the compounds of formula (1a) herein, the compounds are advantageously selective α4β1 inhibitors.

The compounds are of use in modulating cell adhesion and in particular are of use on the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.5 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols R, $R^1$–$R^3$, $R^a$, $R^b$, $L^1$, $Alk^1$, $Alk^2$, m, r, s and Het when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be obtained by hydrolysis of an ester of formula (2):

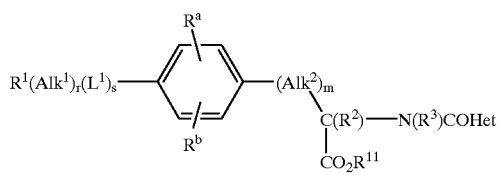

(2)

where $R^{11}$ is an alkyl group.

The hydrolysis may be performed using either an acid or a base depending on the nature of $R^{11}$, for example an organic acid such as trifluoracetic acid or an inorganic base such as lithium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (2) may be prepared by coupling an amine of formula (3):

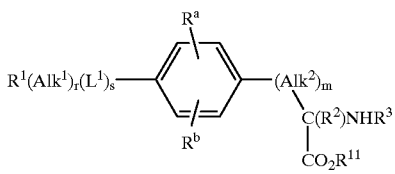

(3)

(where $R^{11}$ is as just described) or a salt thereof with an acid of formula (4):

$$HetCO_2H \qquad (4)$$

or an active derivative thereof.

Active derivatives of acids of formula (4) include anhydrides, esters and halides. Particular esters include pentafluorophenyl or succinyl esters.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around –30° C. to around ambient temperature, optionally in the presence of a base, e.g. an organic base such as an amine, e.g. triethylamine, pyridine, or dimethylaminopyridine, or a cyclic amine, such as N-methylmorpholine.

Where an acid of formula (4) is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine of formula (3).

Intermediates of formulae (2), (3) and (4), or compounds of formula (1), may be manipulated to introduce substituents to aromatic or heteroaromatic groups or modify existing substituents in groups of these types. Typically, such manipulation may involve standard substitution approaches employing for example alkylation, arylation, heteroarylation, acylation, thioacylation, halogenation, sulphonylation, nitration, formylation or coupling reactions. Alternatively, exisitng substituents may be modified for example by oxidation, reduction or cleavage reactions. Particular examples of such reactions are given below. Where these are described in relation to the generation of the group $R^1(Alk^1)_r(L^1)_s$—, it will be appreciated that each reaction may also be used to introduce or modify $R^5$ and/or $R^6$ substituents as appropriate.

Thus in one example, a compound wherein $R^1(Alk^1)_r(L^1)_s$— is a —$L^1$H group may be alkylated, arylated or heteroarylated using a reagent $R^1(Alk^1)_rX$ in which $R^1$ is other than a hydrogen atom and X is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, a compound where $R^1(Alk^1)_r(L^1)_s$ is a —$L^1$H group is a hydrogen atom may be functionalised by acylation or thioacylation, for example by reaction with a reagent $R^1(Alk^1)_rL^1X$ [wherein $L^1$ is a —C(O)—, C(S)—, —$N(R^4)C(O)$— or $N(R^4)C(S)$— group], in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature, or by reaction with $R^1(Alk^1)_rCO_2H$, $R^1(Alk)_4COSH$ or an activated derivative thereof, for example as described above for the preparation of esters of formula (2).

In a further example a compound may be obtained by sulphonylation of a compound where $R^1(Alk^1)_r(L^1)_s$ is an —OH group by reaction with a reagent $R^1(Alk^1)_rL^1Hal$ [in which $L^1$ is —S(O)— or —$SO_2$— and Hal is a halogen atom such as chlorine atom] in the presence of a base, for example an inorganic base such as sodium hydride in a solvent such as an amide, e.g. a substituted amide such as dimethylformamide at for example ambient temperature.

In another example, a compound where $R^1(Alk^1)_r(L^1)_s$ is a —$L^1$H group, may be coupled with a reagent $R^1OH$ (where $R^1$ is other than a hydrogen atom) or $R^1Alk^1OH$ in a solvent such as tetrahydrofuran in the presence of a phosphine, e.g. triphenylphosphine and an activator such as diethyl, diisopropyl- or dimethylazodicarboxylate to yield a compound containing a $R^1(Alk^1)_rO$— group.

In a further example, ester groups —$CO_2R^4$ or —$CO_2Alk^4$ in compounds of formula (1) may be converted to the corresponding acid [—$CO_2H$] by acid- or base-catalysed hydrolysis depending on the nature of the grousp $R^4$ or $Alk^4$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —$OR^7$ [where $R^7$ represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^7$ group (where $R^7$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^4$ or $CO_2R^4$] or aldehyde [—CHO] by reduction, using for example a complex metal hydride such as lithium aluminium hydride or sodium borohydride in a solvent such as methanol.

In another example, alcohol —OH groups in compounds of formula (1) may be converted to a corresponding —$OR^3$ group by coupling with a reagent $R^7OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in compounds of the invention, for example when present in the linker group $L^1$ may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature.

Intermediates of formulae (3) and (4), $R^1(Alk^1)_rX$, $R^1(Alk^1)_rL^1X$, $R^1(Alk^1)_rCO_2H$, $R^1OH$ and $R^1Alk^1OH$ are either known compounds or may be prepared from known starting materials by use of analogous processes to those used for the preparation of the known compounds and/or by treating known compounds by one or more of the alkylation, acylation and other manipulations described herein, such as particularly described for the preparation of the Intermediates in the exemplification selection hereinafter.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The disastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. All temperatures are in °C. The following abbreviations are used:

EDC — 1-(3-dimethylaminopropyl)3-ethycarbodiimide;
DMF — dimethylformamide;         DMSO — dimethylsulphoxide;
HOBT — 1-hydroxybenzotriazole;   THF — tetrahydrofuran;
TFA — trifluoroacetic acid;      NMM — N-methylmorpholine;
DCM — dichloromethane;           Ph — phenyl;
BOC — tert-butoxycarbonyl;       EtOAc — ethyl acetate;
MeOH — methanol;                 LDA — lithium diisopropylamide
tyr — tyrosine;                  Ar — aryl;
HetAr — heteroaryl;              pyr — pyridine;
thiopro — thioproline;           Bu — butyl;
Me — methyl;                     app — apparent

INTERMEDIATE 1

2-Chloronicotinoyl-O-(2,6-dichlorobenzyl)-L-tyrosine-methyl ester

A solution of O-(2,6-dichlorobenzyl)-L-tyrosine methyl ester hydrochloride, (1.11 g, 2.84 mmol), 2-chloronicotinic acid (0.45 g, 2.84 mmol), EDC (0.60 g, 3.13 mmol), HOBT (0.46 g, 3.41 mmol) and NMM (0.467 ml, 0.43 g, 4.26 mmol) in DCM (25 ml) was stirred at room temperature for 24 h. The reaction mixture was partitioned between DCM (50 ml) and 10% $NaHCO_3$ solution (30 ml). The organic layer was separated, dried over $MgSO_4$ and the solvent removed under vacuum to give a pale yellow solid that was recrystallized from EtOAc/hexane to give the title compound as an off white solid (1.14 g, 81%), $\delta H$ ($CDCl_3$) 8.46 (1H, dd, J 2.0, 4.7Hz), 8.05 (1H, dd, J 2.0, 7.6Hz), 7.34 (2H, m), 7.25 (2H, m), 7.11 (2H, m), 6.96 (3H, m), 5.24 (2H, s), 5.06 (1H, m), 3.80 (3H, s) and 3.24 (2H, m).

INTERMEDIATE 2

2-Thio(S-2,5-dimethoxyphenyl)nicotinolyl-O-(2,6-dichlorobenzyl)-L-tyrosine methyl ester A solution of O-(2,6-dichlorobenzyl)-L-tyrosine methyl ester hydrochloride (0.78 g, 2.0 mmol), EDC (0.42 g, 2.2 mmol) HOBT (0.32 g, 2. 4 mmol) and NMM (0.55 ml, 0.50 g, 5.0 mmol) in DMF (10 ml) was treated with a solution of 2-thio(2,5-dimethoxyphenyl)nicotinic acid (0.58 g, 2.0 mmol) in DMF (2 ml) and stirred for 16 h at room temperature. Solvent was removed in vacuo and the residue was partitioned between EtOAc (50 ml) and 10% hydrochloric and (25 ml). The organic layer was separated, washed with 10% $NaHCO_3$ solution (30 ml), dried over $MgSO_4$ and the solvent removed in vacuo to give a yellow oil which was purified by chromatography ($SiO_2$; EtOAc/hexane 1:1) to give the title compound as a while foam (1.14 g, 86%). $\delta H$ ($CDCl_3$) 8.39 (1H, dd, J. 1.9, 4.7Hz), 7.85 (1H, dd, J 1.9, 7.7Hz), 7.47 (1H, J 7.6HJz), 7.37–6.81 (11H, m), 5.18 (2H, s), 5.09 (1H, m), 3.78 (6H, s), 3.53 (3H, s) and 3.25 (2H, m).

INTERMEDIATE 3

2-Mercaptonicotinoyl-O-(2.6-dichlorobenzyl)-L-tyrosine methyl ester

A solution of O-(2,6dichlorobenzyl)-L-tyrosine methyl ester hydrochloride (2.50 g, 6.4 mmol), 2-mercaptonicotinic acid (0.99 g, 6.4 mmol) and NMM (1.41 ml, 1.29 g, 12.8 mmol) in DMF (10 ml) was stirred at room temperature for 64 h. Solvent was removed in vacuo and the residue partitioned between DCM (30 ml) and water (25 ml). The aqueous layer was extracted with DCM (30 ml) and the combined organic layers were washed with 10% $NaHCO_3$ solution (30 ml), dried over $MgSO_4$ and the solvent removed in vacuo to give a brown oil which was purified by chromatography ($SiO_2$; gradient elution, 4:1 EtOAc/hexane to 100% EtOAc) to give the title compound as a yellow foam, (2.92 g, 93%). $\delta H$ ($CDCl_3$) 8.71 (1H, dd, J 1.8, 7.6Hz), 8.05 (1H, s), 7.61 (1H, dd, J 1.8, 6.1 Hz), 7.35 (2H, m), 7.33–7.19 (2H, m), 6.94 (2H, d, J 8.7Hz), 5.22 (2H, s), 4.97 (1H, m), 3.74 (3H, s) and 3.21 (2H, m).

INTERMEDIATE 4

2-Thio(S-4-picolinyl)nicotinolyl-O-(2,6-dichlorobenzyl)-L-tyrosine methyl ester

A solution of intermediate 3 (0.50 g, 1.0 mmol) and 4-picolyl chloride hydrochloride (0.17 g, 1.0 mmol) in DCM (10 ml) was treated with 1,8-diazabicyclo[5.4.0]undec-7-ene (0.31 ml, 0.31 g, 2.0 mmol) and stirred at room temperature for 5 h. The reaction was partitioned between water and DCM, the organic layer separated, dried over $MgSO_4$ and the solvent removed in vacuo to give a yellow gum that was purified by chromatography ($SiO_2$, EtOAc), to give a pale yellow solid, which was recrystallised from EtOAc/hexane (1:1) to give the title compound as an off white solid (0.30 g, 52%). $\delta H$ ($CDCl_3$) 8.47(2H, m), 7.69 (1H, dd, J 1.8, 77Hz), 7.38–7.22 (6H, m), 7.06 (3H, m), 6.90 (2H, m), 6.62 (1H, d, J 7.5Hz), 5.23 (2H, s), 5.03 (1H, m), 4.40 (2H, m), 3.79 (3H, s), 3.28 (1H, dd, J 5.8, 14.1Hz) and 3.19 (1H, dd, J 5.4, 14.1Hz).

INTERMEDIATE 5

2-Thio(S-2,5-dimethoxyphenyl)nicotinoyl-L-4-aminophenylalanine methyl ester

A solution of 4-amino-L-phenylalanine methyl ester dihydrochloride (0.53 g, 2.0 mmol), EDC (0.42 g, 2.2 mmol) HOBT (0.32 g, 2.4 mmol) and NMM (0.66 ml, 0.61 g, 6.0 mmol) in DMF (10 ml) was treated with a solution of 2-thio)2,5-dimethoxyphenyl)nicotinic acid (0.58 g, 2.0 mmol) in DMF (2 ml) and stirred for 64 h at room temperature. The solvent was removed in vacuo, and the residue partitioned between DCM (30 ml) and water (20 ml). The organic layer was separated, washed with 10% $NaHCO_3$ (20 ml) solution, dried over $MgSO_4$ and the solvent evaporated in vacuo to give a brown gum which was purified by chromatography ($SiO_2$; EtOAc) to give the title compound as a yellow foam (0.67 g, 72%), $\delta H$ ($CDCl_3$) 8.35 (1H, dd, J 1.8, 4.8Hz), 7.81 (1H, dd, J 1.9, 7.7Hz), 7.41 (1H, d, J 7.6Hz), 7.12 (1H, d, J 3.0Hz), 7.07–6.81 (5H, m), 6.49 ) 2H, d, J 8.4Hz), 5.00 (1H, m), 3.76 (3H), s), 3.74 (3H, s, 3.55 (3H, s) and 3.14 (2H, m).

INTERMEDIATE 6

2-Thio(S-2,5-dimethoxyphenyl)nicotinoyl-(N-2,6-dichlorobenzoyl)-L-4-aminophenylalanine methyl ester A solution of intermediate 5 (0.68 g, 1.5 mmol) and NMM (0.53 ml, 0.49 g, 4.8 mmol) in DCM (20 ml) was treated with 2,6-dichlorobenzoyl chloride (0.23 ml, 0.33 g, 1.6 mmol) and the reaction stirred for 16 h at room temperature, then partitioned between DCM (50 ml) and 10% NaHCO$_3$ solution (30 ml). The organic layer was separated, dried over MgSO$_4$ and the solvent evaporated in vacuo to give an off-white solid that was triturated with EtOAc/diethyl ether (2:1) to give the title compound as an off-white solid (0.44 g, 46%). δH (MeOH-d$^4$) 8.28 (1H, dd, J 1.8, 4.9Hz), 7.70 (1H, dd, J 1.8, 7.6Hz), 7.58 (2H, d, J 8.6Hz), 7.48–7.38 (3H, m), 7.30 (2H, d, J 8.6Hz), 7.27 (1H, dd, J 4.9, 7.7Hz), 7.01 (1H, dd, J 1.1, 2.3Hz), 6.93 (2H, m), 4.87 (1H, m), 3.77 (3H, s), 3.75 (3H, s), 3.60 (3H, s), 3.32 (1H, m) and 3.13 (H, dd, J 8.6, 14.0Hz).

INTERMEDIATE 7

O-(2,6-dichlorobenzyl)-N-(4-acetyl-1,2,5-trimethyl-3-pyrroyl)-L-tyrosine methyl ester NMM (155 mg, 169 μl, 1.54 mmol), HOBT (227 mg, 1.68 mmol), 4-acetyl-1,2,5-trimethylpyrrole-3-carboxylic acid (300 mg, 1.54 mmol) and EDC (295 mg, 1.54 mmol) were added sequentially to a stirred solution of O-(2,6-dichlorobenzyl)-L-tyrosine methyl ester hydrochloric (546 mg, 1.40 mmol) in dry DMF (15 ml). The reaction was stirred at room temperature under N$_2$ for 18 h. The solvent was removed in vacuo and the residue partitioned between EtOAc (50 ml), and 10%aqueous Na$_2$CO$_3$ (40 ml). The phases were separated and the queous phase extracted with EtOac (2×25 ml). The combined organic extracts were washed consecutively with 5% aqueous hydrochloric acid (20 ml), 10% aqueous Na$_2$SO$_3$ (20 ml) and brine (10 ml), dried (Na$_2$SO$_4$) and evaporated in vacuo. The obtained orange foam (0.6 g) was chromatographed (silica; 50% EtOAc/Hexane→100% EtOAc) affording the title compound as a white foam (380 mg, 51%); 'Hnmr (d$^6$DMSO) 8.53 (1H, d, J 8Hz, NH), 7.57–7.43 (3H, m's, aryl-H), 7.22 (2H, d, J 8.5Hz), aryl-H), 6.95 (2H, d, J 8.5 Hz, aryl-H), 5.18 (2H, br s, CH$_2$-O), 4.67 (1H, m, α-tyr-H), 3.66 (3H, s, Me-O), 3.34 (3H, s, Me-N), 3.12 (1H, dd, J 4.1, 13.8Hz, CH$_A$B$_B$Ar), 2.90 (1H, dd, J 11.3 13.8Hz, CH$_2$H$_B$Ar), 2.32 (3H, s, MeCO), 2.0 (3H, s, pyrrole-Me) and 1.94 (3H, s, pyrrole-Me). m/z (ES+60V) 531 (MH+, 100 ), 533 (MH+, 75) 553( MNz+, 15%).

INTERMEDIATE 8

2-Chloronicotinyl-(N-2,6-dichlorobenzoyl)-L-4-aminophenylalanine methyl ester

EDC (270 mg, 1.5 mmol) was added to a stirred solution of (N-2,6-dichlorobenzoyl)-L-4-aminophenylalanine methyl ester (500 mg, 1.3 mmol), 2 chloronicotinic acid (200 mg, 1.3 mmol), HOBT (190 mg, 1.5 mmol) and NMM (423 μl, 3.9 mmol) in anhydrous DMF (2 ml) at 0°. The DMF solution was stirred overnight at room temperature then the DMF was evaporated in vacuo. The residue was taken up in DCM (50 ml), washed with water (3×10 ml), saturated aqueous NaHCO$_3$ (2×10 ml)and water (2×10 ml), dried (Na$_2$SO$_4$) and evaporated in vacuo. The residue was purified by chromatography (SiO$_2$; 1:1 EtOAc: hexane) to give the title compound as a white foam (450 mg, 80%). δH (CDCl$_3$), 8.50 (1H, m, pyr H), 8.05 (1H, d, J 9.2Hz, pyrH), 7.58 (2H, d, J 8.5Hz, ArH), 7.48 (1H, br s; NH), 7.36–7.24 (3H, m, 2ArH, 1pyrH), 7.21 (2H, d, J 8.5 Hz, 2 ArH), 7.12 (1H, d, J 6.6Hz, NH), 5.06–5.18 (1H, m, CHαtyr). 3.81 (3H, s, CO$_2$Me) and 3.39–3.18 (2H, m, CH$_2$Ar).

INTERMEDIATE 9

Methyl-2-thio(S-acetate)nicotinoyl-O-(2,6-dichlorobenzyl)-L-tyrosine methyl ester A solution of intermediate 3 (370 mg, 0.75 mmol) in anhydrous DMF (2 ml) was added to a suspension of sodium hydride (80%, in oil, 33 mg, 0.83 mmol) in anhydrous DMF (3 ml) at 0°. The mixture was stirred for 10 min at room temperature, then recooled to 0°. Methyl bromoacetate (115 mg, 0.76 mmol) was added dropwise, then the mixture was stirred overnight at room temperature. The mixture was quenched with water (0.5 ml) and the DMF evaporated in vacuo. The residue was dissolved in EtOAc, washed with water (3×10 ml), dried (Na$_2$SO$_4$) and evaporated in vacuo. The residue was purified by chromatography (SiO$_2$; EtOAc/hexane 1:1) to give the title compound as a white solid (360 mg, 85%). δH (CDCl$_3$) 8.45 (1H, m, pyrH), 7.71 (1H, d, J 7.7, pyrH), 7.35 (2H, d, J 73.Hz, 2ArH), 7.28–6.9 (6H, m, 5ArH), 1 pyrH), 6.71 (1H, d, J 7.5Hz, NH), 5.24 (2H, s, OCH$_2$Ar), 5.08–5.03 (1H, m, CHα tyr), 3.96 (2H, s, SCH$_2$), 3.78 (3H, s, CO$_2$CH$_3$), 3.71 (3H, s, CO$_2$CH$_3$), 3.31 (1H, dd, J 14, 5.4Hz, CH$_A$H$_B$Ar) and 3.21 (1H, dd, J 14, 5.2Hz, CH$_A$H$_B$Ar).

INTERMEDIATE 10

2-Thio(S-methyl)nicotinoyl-O-(2,6-dichlorobenzyl)-L-tyrosine methyl ester

EDC (540 mg, 3 mmol) was added to a stirred solution of (O-2,6-dichlorobenzyl)-L-tyrosine methyl ester (1 g, 2.6 mmol), 2 methylmercaptonicotinic acid (433 mg, 2.6 mmol), HOBT (364 mg, 2.6 mmol) and NMM (846 μl, 7.8 mmol) in anhydrous DMF (4 ml) at 0°. The DMF solution was stirred overnight at room temperature, then the DMF was evaporated in vacuo. The residue was taken up in DCM (70 ml), washed with water (3×15 ml), saturated aqueous NaHCO$_3$ (2×15 ml) and waster (2×15 ml), dried (Na$_2$SO$_4$) and evaporated in vacuo. The residue was purified by chromatography (SiO$_2$; EtOAc) to give the title compound as a white solid (1.2 gm, 92%), δH (CDCl$_3$) 8.42 (1H, dd, J 1.7, 4.8, 1 pyrH), (, 7.67 (1H, dd, J 1.7, 7.6, 1pyrH), 7.31 (2H, d, J 8.5, ArH), 7.18 (1H, dd, J 2.3, 8.5, ArH), 7.09 (3H, d, plus broad peak, J 8.6, 2ArH, 1NH), 6.97 (1H, m, 1 pyrH), 6.88 (2H, d, J 8.6, 2ArH), 5.18 (2H, s, OCH$_2$Ar), 4.96 (1H, m, CHαtyr), 3.72 (3H, s, OCH$_3$), 3.25–3.04 (2H, m, CH$_2$Ar) and 2.47 (3H, s, SCH$_3$). m/z (ESI, GOU) 505 (MH+).

INTERMEDIATE 11

Ethyl 3-(4-{[(4-methoxybenzyl)oxy]carbonyl}-2-[(diphenylmethylene)amino]propanoate N-(Diphenylmethylene) glycine ethyl ester (6.6 g, 24.6 mmol) and potassium carbonate (6.8 g, 49 mmol) were added to a solution of 4-methyloxybenzyl- 4-bromomethyl) benzoate (8.2 g, 24.6 mmol) in acetonitrile (200 ml). The mixture was heated at reflux overnight, then filtered and the solvent removed in vacuo to give the title compound as a yellow oil (13.55 g). δH (CDCl$_3$, 300 MHz) 7.8 (2H, d, J 9.0Hz), 7.5 (10H, m), 7.3 (2H, d, J 9.0Hz), 6.9 (2H, d), 6.6 (2H, m), 5.23 (2H, s), 4.1 (3H, m), 3.7 (3H, s), 3.2 (2H, m) and 1.2 (3H, m); m/z (ESI) 522 (MH+).

INTERMEDIATE 12

Ethyl 2-amino-3-(4{[(4-methoxybenzyl)oxy]carbonyl}phenyl) propanoate

Hydrochloric acid (2M, 15.83 ml, 1.5 eq), was added to a solution of intermediate 11 (11.0 g, 21.12 mmol) in THF (30 ml). After 20 min the reaction mixture was basified to pH7 with NaHCO$_3$ and the solvent removed in vacuo. The residue was taken up to EtOAc (300 ml) and washed with water (200 ml) and brine (200 ml), dried (MgSO$_4$) and evaporated in vacuo. Chromatography (SiO$_2$; EtOAc) gave the title compound as a yellow oil (4.91 g, 65%). δH (CDCl$_3$, 300MHz) 7.88 (2H, d, J 8.0Hz), 7.4 (4H, dd), 7.0 (2H, d, J 8.0Hz), 5.25 (2H, s), 4.05 (2H, q), 3.7 (3H, s), 3.57 (1H, t) 2.87 (2H, m) and 1.1 (3H, t), m/z (ESI) 358 (MH+).

INTERMEDIATE 13

Ethyl-2-{[(2-chloro-3-pyridinyl)carbonyl]amino}-3-(4-{[(4-methoxybenzyl)oxy]carbonyl}phenyl) propanoate EDC;HCl (591 mg, 3.08 mmol) and HOBT (416 mg, 3.08 mmol) were added to a solution of intermediate 12 (1.0 g, 2.8 mmol), 2-chloronicotinic acid (450 mg, 2.86 mmol) and NMM (370 μl, 3.36 mmol) in DMF (30 ml). The reaction mixture was stirred overnight at room temperature. The solvent was removed in vacuo and the residue partitioned between EtOAc (300 ml) and NaHCO$_3$ solution (300 ml). The organic phase was washed with citric acid (10%, 2×200 ml), NHCO$_3$ solution (200 ml) and brine (300 ml), dried (MgSO$_4$) and concentrated in vacuo to give the title compound as a yellow oil (1.35 g, 98%). δH (CDCl$_3$, 300 MHz) 9.12 (1H, d, J 8.0Hz), 8.47 (1H, m), 7.91 (2H, d, J 8.0Hz), 7.6 (1H, dd), 7.45 (5H, m), 6.95 (2H, d, J 8.0Hz), 4.67 (1H, m), 4.15 (2H, m), 3.75 (3H, s), 3.31 (1H, m), 3.23 (1H, m) and 1.17 (3H, s); m/z (ESI) 497 (MH+).

INTERMEDIATE 14

Ethyl 2-{[(2-chloro-3-pyridinyl)carbonyl]amino}-3-[4-(carboxyl)phenyl]propanoate TFA (20 ml) was added to a solution of intermediate 13 (1.36 g, 2.75 mmol) in toluene (20 ml). The reaction mixture was stirred for 30 min at room temperature. The white solid obtained was recrystallised (EtOAc/hexane) to give the title compound (1.04 g, 100%). δH (CDCl$_3$, 300 MHz) 12.84 (1H, br s), 9.1 (1H, d, J 8.0Hz), 8.47 (1H, m), 7.87 (2H, d, J 8.0HZ), 4.1 (2H, m), 3.2 (1H, m), 3.07 (1H, m) and 1.17 (3H, m); m/z (ESI) 377 (MH+).

INTERMEDIATE 15

Ethyl 2-{[(2-chloro-3-pyridinyl)carbonyl]amino}-3-(4-{(2,6-dichloroanilino)carbonyl}phenyl) propanoate Carbon tetrachloride (5 ml) was added to a suspension of intermediate 14 (1.04 g, 2.76 mol) and triphenylphosphine (0,87 g, 3.31 mmol) in acetonitrile. The reaction mixture was stirred for 2 h at room temperature. 2,6-Dichloroaniline (0.89 g, 5.52 mmol) and NMM (455 μl, 4.14 mmol) were added and the mixture stirred for a further 48 h at room temperature. The solvent was removed in vacuo and the residue partitioned between water and EtOAc. The aqueous layer was extracted with EtOAc (x 2) and the combined organic extracts washed with water (x 2) and saturated aqueous NaHCO$_3$ (x2), dried (Na$_2$SO$_4$) and concentrated in vacuo. Chromatography (SiO$_2$; EtOAc/hexane 50:50) gave the title compound (924 mg) δH (CDCl$_3$, 300MHz) 8.46 (1H, s), 8.05 (1H, d, J 7.4Hz), 7.89 (2H, d, J 7.9Hz), 7.69–7.10 (8H, m), 5.11 (1H, dt, J 6.7, 5.8Hz), 4.25 (2H, q, J 71Hz), 3.42 (1H, dd, J 13.9, 5.8Hz), 3.31 (1H, dd, J 13.9, 5.8Hz) and 1.30 (3H, t, J 7.1Hz).

INTERMEDIATE 16

Methyl 4-[2(2,6-dichlorophenyl)-2-hydroxyethyl] benzoate

A solution of methyl 4-(bromomethyl)benzoate (2.0 g, 8.7 mmol) in THF (4.4 ml) was added slowly to cut zinc foil (683 mg, 10.44 mmol) which had been activated with 1,2-dibromoethane (80 mg). After 3 h of stirring at room temperature 2 ml of the solution was referred to a solution of copper cyanide (396 mg, 4.4 mmol) and lithium chloride (356 mg, 8.4 mmol) in THF (4 ml) cooled to −78°. This solution was warmed to −20° and then cooled back to −78°. Boron trifluoride etherate (983 μl, 8 mmol) was then added followed by 2,6-dichlorobenzaldehyde (0.56 g, 3.2 mmol) in THF (1 ml). The reaction was stirred for 2 h and then allowed to warm slowly to room temperature. Water (20 ml) was then added and the reaction mixture extracted into EtOAc (3×25 ml) and the combined organics dried (Na$_2$SO$_4$) and evaporated. Purification by column chromatography (SiO$_2$; hexane:EtOAc. 4:1) gave the title compound as a colourless oil (863 mg, 83%). δH (CDCl$_3$) 7.95 (2H, m, ArH), 7.93–7.26 (4H, m, ArH), 7.17–7.12 (1H, m, ArH), 5.73–5.65 (1H, m, CH), 3.91 (3H, s, CO$_2$Me), 3.43 (1H, dd, J 13.5, 8.4 Hz, CH$_A$B$_{4L}$) and 3.28 (1H, dd, J 13.5, 6.3Hz, CH$_A$H$_B$), m/z (ESI, 60V) 325(MH+).

INTERMEDIATE 17

Methyl 4-[2-{[tert-butyl(dimethyl)silyl]oxy}-2-(2,6-dichlorophenyl) ethyl]benzoate To a solution of intermediate 16 (20 g, 6.15 mmol) in DCM (10 ml) cooled to 0° was added 2,4,6-collidine (2.03 ml, 15.39 mmol). Afte r15 min tert-butyldimethylsilyltrifluoromethanesulphonate (2.12 ml, 9.23 mmol) was added. The reaction mixture was stirred overnight at room temperature then diluted with DCM (100 ml) and washed with 1M hydrochloric acid (50 ml), waster (50 ml) and brine (50 ml), dried (Na$_2$SO$_4$) and evaporated under reduced pressure. Purification by column chromatography (SiO$_2$; hexane:EtOAc, 5:1) gave the title compound as a pale pink oil (2.67 g, 100%). δH (CDCl$_3$) 7.94 (2H, d, J 6.5Hz, ArH), 7.33, 7.21 (4H, m, ArH), 7.13–7.07 (1H, m, ArH), 5.58 (1H, dd, J 9.4, 4.6Hz, CH), 3.90 (1H, s, CO$_2$Me), 3.46 (1H, dd, J 13.1, 9.4Hz, CH$_A$H$_B$), 3.04 (1H, dd, J 13.1, 4.6Hz, CH$_A$H$_B$), 0.74 (9H, s, Si$^t$Bu), −0.31 (3H, s, SiMe) and −0.32 (3H, s, SiMe); m/z (ESI, 60V) 361 (MH+).

INTERMEDIATE 18

4-[2-{[Tert-butyl(dimethyl)allyl]oxy}-2-(2,6-dichlorophenyl)ethyl]benzylalcohol

Lithium aluminium hydride (1M solution in THF, 6.46 ml, 6.46 mmol) was added to an ice cold solution of intermediate 17 (2.67 g, 6.15 mmol) in THF (20 ml). The reaction mixture was stirred for 1 h then quenched with the addition of water and extracted into CDM (3×50 ml), dried (Na$_2$SO$_4$) and evaporated under reduced pressure. Purification by column chromatography (SiO$_2$; hexane:EtOAc, 4:1) gave the title compound as a colourless oil (2. g, 87%) δH 7.32–7.06 (7H, m, ArH), 5.56 (1H, dd, J 9.3, 4.7Hz, CH$_2$CH), 4.65 (2H, d, J 5.9Hz, CH$_2$O), 3.39 (1H, dd, J 13.2, 9.3Hz, CH$_A$H$_B$), 3.01 (1H, dd, J 13.2, 4.7Hz, CH$_A$H$_B$), 0.75 (9H, s, Si$^t$Bu), −0.29 (3H, s, SiMe) and −0.31 (3H, s, SiMe); m/z (ESI, 60V) 433 (MH+).

INTERMEDIATE 19

4-[2-{[Tert-butyl(dimethyl)silyl]oxy}-2-(2,6-dichlorophenyl)ethyl]benzylbromide

A solution of triphenylphosphine (643 mg, 3.21 mmol) in DCM (2 ml) was added to a solution of carbon tetrabromide (1.42 g, 3.73 mmol) and intermediate 18 (1.10 g, 2.67 mmol)

in DCM (3 ml) and stirred at room temperature for 24 h. Ether (100 ml) was added and the solid precipitate formed removed by filtration. The filtrate was evaporated under reduced pressure and the residue purified by column chromatography (SiO$_2$: 8:1, hexane:EtOAc) to give the title compound (1.20 g, 95%). δH (CDCl$_3$) 7.32–7.07 (7H, m, ArHO, 5.54 (1H, dd, J 9.5, 4.4Hz, CH$_2$CH), 4.49 (2H, s, CH$_2$Br), 3.39 (1H, dd, J 13.2, 9.5Hz, CH$_A$H$_B$), 2.96 (1H, dd, J 13.2,4.4Hz, CH$_A$H$_B$), 0.73 (9H, s, Si$^t$Bu), −0.31 (3H, s, SiMe) and −0.32 (3H, s, SiMe); m/z (ESI, 60V) 474 (MH+).

INTERMEDIATE 20

4-[2-{[Tert-butyl(dimethyl)silyl]oxy}-2-(2,6-dichlorophenyl)ethyl]phenylalanine ether ester To a solution of ethyl N-(diphenylmethylene)glycinate (2.63 g, 9.81 mmol) in THF (50 ml) cooled to −78° was added lithium diisopropylamine (2M in heptane/THF/ethylbenzene, 5.64 ml, 11.28 mmol). The solution was stirred for 45 min. Intermediate 19 (4.20 g, 8.92 mmol) in THF (20 ml) was then added dropwise. The reaction mixture was stirred for 2 h at −78° and then warmed to room temperature. EtOAc (100 ml) was added and the mixture washed with water (75 ml) and brine (75 ml), dried (Na$_2$SO$_4$) and evaporated under reduced pressure. The residue was then taken up in acidic ethanol and stirred for 10 min. The volatiles were then removed and the residue partitioned between EtOAc (150 ml) and saturated aqueous Na$_2$CO$_3$ (100 ml). The aqueous layer was extracted several times with EtOAc and the combined organics dried (Na$_2$SO$_4$) and evaporated under reduced pressure. The remaining residue was purified by column chromatography (SiO$_2$; EtOAC) to give the title compound as a colourless oil (3.95 g, 95%). δH (CDCl$_3$) 7.32–7.05 (7H, m, ArH), 5.52 (1H, dd, J 9.4, 4.6 Hz, CHOSi), 4.18 (2H, q, J 7.1 Hz, CO$_2$CH$_2$CH$_3$), 3.68 (1H, dd, J 7.9, 5.1 Hz, CHNH$_2$), 3.35 (1H, dd, J 13.2, 9.4 Hz, CHOSiCH$_A$H$_B$), 3.07 (1H, dd, J 13.5, 5.1 Hz, CHNH$_2$CH$_A$H$_B$), 2.95 (1H, dd, J 13.2, 4.6 Hz, CHOSiCH$_A$H$_B$), 2.95 (1H, dd, J 13.2, 4.6 Hz, CHOSiCH$_A$H$_B$), 2.82 (1H, dd, J 13.5, 7.9 Hz, CHNH$_2$CH$_A$H$_B$), 1.53 (2H, br s, NH$_2$), 1.27 (3H, t, J 7.1 Hz, CO$_2$CH$_2$CH$_3$), 0.74 (9H, s, Si$^t$Bu) and −0.32 (6H, s, SiMe$_2$); m/z (ESI, 60V) 496 (MH$^+$).

INTERMEDIATE 21

{4-[2-{[Tert-butyl(dimethyl)silyl]oxy}-2-(2,6-dichlorophenyl)ethyl}-(N-2-chloronicotinoyl) phenylalanine ethyl ester To a solution of Intermediate 20 (1.50 g, 3.2 ommol) and 2-chloronicotinic acid (504 mg, 3.20 mmol) in DCM (75 ml) at room temperature was added NMM (386 μl, 3.53 mmol), EDC (675 mg, 3.53 mmol) and HOBT (477 mg, 3.53 mmol). The reaction mixture was stirred overnight at room temperature and then diluted with DCM (50 ml) and washed with saturated aqueous Na$_2$CO$_3$ (50 ml), water (50 ml) and brine (50 ml), dried (Na$_2$SO$_4$) and evaporated under reduced pressure. The residue was purified by column chromatography (SiO$_2$; EtOAc) to give the title compound as a white solid (1.72 g, 85%). δH (CDCl$_3$) 8.41–8.38 (1H, m, NH), 8.01–7.96 (1H, m, ArH), 7.29–6.97 (9H, m, ArH), 5.47 (1H, dd, J 9.2, 4.7 Hz, CHOSi), 5.24–4.96 (1H, m, CHNH), 4.19 (2H, qd, J 7.1, 1.1 Hz, CO$_2$CH$_2$CH$_3$), 3.34–3.14 (4H, m, CH$_2$×2), 1.27 (3H, td, J 7.1, 1.3 Hz, CO$_2$CH$_2$CH$_3$), 0.69 (s) and 0.66 (s); together (9H, Si$^t$Bu), and −0.38 (s) and −0.40 (s); together (6H, SiMe$_2$); 659 (M$^+$+Na$^+$).

INTERMEDIATE 22

(N-2-Chloronicotinoyl)-4-[2-(2,6-dichlorophenyl)-2-hydroxyethyl]phenylalanine ethyl ester Tetrabutylammonium fluoride (1M in THF, 4.7 ml, 4.70 mmol) was added to a solution of Intermediate 21 (1.50 g, 2.35 mmol) in THF (75 ml) at room temperature. The reaction mixture was stirred for 2 h and then the THF removed and the residue partitioned between EtOAc and water. The layers were separated and the aqueous layer extracted with EtOAc. The combined organics were dried (Na$_2$SO$_4$) and evaporated under reduced pressure. Purification of the residue by column chromatography (SiO$_2$; MeOH:DCM, 5:95) gave the title compound as a pale brown oil (1.03 g, 84%) δH (CDCl$_3$) 8.31–8.29 (1H, m, NH), 7.86–7.82 (1H, m, ArH), 7.25–6.96 (9H, m, ArH), 5.54–5.49 (1H, m, CH), 4.94–4.88 (1H, m, CH), 4.11 (2H, qd, J 7.1, 2.0 Hz, CO$_2$CH$_2$CH$_3$), 3.28–3.03 (4H, m, 2×CH$_2$) and 1.19 (3H, td, J 7.1, 1.1 Hz, CO$_2$CH$_2$CH$_3$); m/z (ESI, 60V) 521 (MH$^+$).

INTERMEDIATE 23

(N-2-Chloronicotinoyl)-{4-[2-(2,6-dichlorophenyl)-2-oxoethyl]}phenylalanine ethyl ester To a solution of Intermediate 22 (300 mg, 0.58 mmol) in acetone (20 ml) was added Jones' Reagent dropwise until an orange colour persisted. i-Propyl alcohol was added to use up excess reagent and then the solution was basified by the addition of saturated aqueous Na$_2$CO$_3$ solution. The solution was then decanted from the solids and the acetone removed in vacuo. The remaining aqueous solution was then extracted with ether (×2) and the combined organics dried (Na$_2$SO$_4$) and evaporated under reduced pressure. The residue was purified by column chromatography (SiO$_2$; hexane:EtOAc, 3:2) to give the title compound as a colourless oil (200 mg, 67%). δH (CDCl$_3$) 8.40 (1H, dd, J 4.8, 2.0 Hz), 7.94 (1H, dd, J 7.7, 2.0 Hz), 7.38–7.11 (8H, m, ArH), 7.02 (1H, d, J 7.5 Hz, ArH), 4.19 (2H, q, J 7.2 Hz, CO$_2$CH$_2$CH$_3$), 4.09 (2H, s, CH$_2$CO), 3.28 (1H, dd, J 14.0, 5.9 Hz, CH$_A$H$_B$), 3.18 (1H, dd, J 14.0, 6.1 Hz, CH$_A$H$_B$) and 1.26 (5H, t, J 7.2 Hz, CO$_2$CH$_2$CH$_3$); m/z (ESI, 60V) 519 (MH$^+$).

INTERMEDIATE 24

Methyl 4-[(E)-2-(2,6-dichlorophenyl)ethenyl] benzoate

A solution of Intermediate 16 (2.0 g, 6.15 mmol) in toluene (25 ml) containing p-toluenesulphonic acid (100 mg) was heated to reflux in a Dean-Stark apparatus for 4 h. Toluene was then removed under reduced pressure and the residue purified by column chromatography (SiO$_2$; hexane:EtOAc, 5:1) to give the title compound as an off white solid (1.64 g,87%); δH (CDCl$_3$) 8.05 (2H, d, J 8.3 Hz), 7.60 (2H, d, J 8.3 Hz, ArH), 7.36 (2H, d, J 8.0 Hz), 7.21 (2H, d, J 1.7 Hz), 7.15–7.10 (1H, m), and 3.93 (3H, s, CO$_2$CH$_3$); m/z (ESI, 60V) 329 (MH$^+$).

INTERMEDIATE 25

4-[(E)-2-(2,6-Dichlorophenyl)ethenyl]benzyl alcohol

To an ice cold solution of Intermediate 24 (1.56 g, 5.08 mmol) in THF (20 ml) was added lithium aluminum hydride (1M in THF, 5.34 ml, 5.34 mmol). The reaction mixture was stirred for 30 min and then quenched by the addition of water (10 ml). The resulting biphasic solution was filtered through Celite® and then extracted with DCM (2×50 ml). The combined organics were dried (Na$_2$SO$_4$) and evaporated under reduced pressure to give the title compound as a colourless oil which solidified on standing (1.5 g, 99%). δH (CDCl$_3$) 7.55 (2H, d, J 8.2 Hz), 7.42–7.33 (4H, m), 7.20–7.08 (3H, m) and 4.75 (2H, d, J 5.3 Hz, CH$_2$); m/z (ESI, 60V) 301 (M$^+$+Na$^+$).

INTERMEDIATE 26

4-[(E)-2-(2,6-Dichlorophenyl)ethenyl]benzyl bromide

A solution of triphenylphosphine (1.58 h, 6.04 mmol) in DCM (10 ml) was added to a solution of Intermediate 25 (1.40 g, 5.03 mmol) and carbon tetrabromide (2.33 g, 7.04 mmol) in DCM (10 ml). The resulting solution was stirred for 1 h and then diluted with ether (150 ml) and the resulting solid removed by filtration. The filtrate was then evaporated under reduced pressure and the resulting residue purified by column chromatography ($SiO_2$; hexane:EtOAc, 6:1) to give the title compound as a colourless oil (1 g, 49%). $\delta$H ($CDCl_3$) 7.55 (2H, d, J 8.3 Hz), 7.44–7.32 (3H, m), 7.23–7.09 (4H, m) and 4.53 (2H, s, $CH_2$); m/z (ESI, 60V) 342 ($MH^+$).

INTERMEDIATE 27

4-[(E)-2-(2,6-Dichlorophenyl)ethenyl]phenylalanine ethyl ester

To a solution of ethyl N-(diphenylmethylene)glycinate (860 mg, 3.21 mmol) in THF (20 ml) cooled to −78° was added lithium diisopropylamine (2M in heptane/THF/ethylbenzene, 1.68 ml, 3.36 mmol). The solution was stirred for 45 min. Intermediate 26 (10 g, 2.92 mmol) in THF (2 ml) was added and the resulting reaction mixture stirred for 2 h at −78° and then warmed to room temperature. EtOAc (100 ml) was added and the mixture washed with water (75 ml) and brine (75 ml), dried ($Na_2SO_4$) and evaporated under reduced pressure. The residue was then taken up in acidic ethanol and stirred for 1 min. The volatiles were then removed and the residue partitioned between EtOAc (150 ml) and saturated aqueous $Na_2CO_3$ (100 ml). The aqueous layer was extracted several times with EtOAc and the combined organics dried ($Na_2SO_4$) and evaporated under reduced pressure. The remaining residue was purified by column chromatography ($SiO_2$; EtOAc) to give the title compound as a colourless oil (860 mg, 81%). $\delta$H ($CCl_3$) 7.47 (2H, d, J 8.1 Hz), 7.32 (2H, d, J 8.1 Hz), 7.21 (2H, d, J 8.2 Hz), 7.19–6.98 (3H, m), 4.18 (2H, q, J 7.1 Hz, $CO_2CH_2CH_3$), 3.71 (1H, dd, J 7.8, 5.3 Hz, CH), 3.10 (1H, dd, J 13.5, 5.3 Hz, $CH_AH_B$) 2.88 (1H, dd, J 13.5, 7.8 Hz, $CH_AH_B$) and 1.26 (3H, t, J 7.1 Hz, $CO_2CH_2CH_3$); m/z (ESI, 60V) 364 ($MH^+$).

INTERMEDIATE 28

(N-2-Chloronicotinoyl)-4-[(E)-2-(2,6-dichlorophenyl)ethenyl]phenylalanine ethyl ester To a solution of Intermediate 27 (860 mg, 2.36 mmol) and 2-chloronicotinic acid (372 mg, 2.36 mmol) in DCM (25 ml) was added NMM (285 μl, 2.60 mmol), EDC (498 mg, 2.60 mmol) and HOBT (352 mg, 2.60 mmol). The resulting solution was stirred for 3 h and then diluted with DCM (50 ml) and brine (50 ml), dried ($Na_2SO_4$) and evaporated under reduced pressure. The residue was purified by column chromatography ($SiO_2$; EtOAc) to give the title compound as a pale yellow oil (1.1 g, 93%). $\delta$H ($CDCl_3$), 8.43 (1H, dd, J 4.8, 2.0 Hz), 8.02 (1H, dd, J 7.6, 2.0 Hz), 7.46 (2H, d, J 8.2 Hz), 7.34–6.92 (9H, m), 5.10–5.03 (1H, m, CH), 4.24 (2H, q, J 7.1 Hz, $CO_2CH_2CH_3$), 3.33 (1H, dd, J 13.9, 5.8 Hz, $CH_AH_B$), 3.24 (1H, dd, J 13.9, 5.8 Hz, $CH_AH_B$) and 1.30 (3H, t, J 7.1 Hz, $CO_2CH_2CH_3$); m/z (ESI, 60V) 503.5 ($MH^+$).

INTERMEDIATE 29

N-(2-Chloronicotinoyl)-L-tyrosine methyl ester

EDC.HCl (2.11 g, 11 mmol) was added to a mixture of L-tyrosine methyl ester hydrochloride (2.32 g, 10 mmol), 2-chloronicotinic acid (1.58 g, 10 mmol), HOBT (1.49 g, 11 mmol) and NMM (2.31 ml, 21 mmol) in DMF (50 ml). The mixture was stirred overnight at room temperature. The solvent was removed in vacuo. the residue dissolved in EtOAc (300 ml) and washed with dilute HCl (100 ml), saturated aqueous $NaHCO_3$ (100 ml), water (3×100 ml) and brine (50 ml), dried ($Na_2SO_4$) and solvent removed in vacuo to give the title compound as a yellow gum (3.27 g, 98%). $\delta$H (DMSO-$d_6$, 300 MHz) 9.21 (1H, s, OH), 9.03 (1H, d, J 7.9 Hz, CONH), 8.45 (1H, dd, J 4.8, 1.9 Hz, pyrH), 7.67 (1H, dd, J 7.4, 1.9 Hz, pyrH), 7.47 (1H, dd, J 7.5, 4.8 Hz, pyrH), 7.05 (2H, d, J 8.5 Hz, ArH), 6.67 (2H, d, J 8.5 Hz, ArH), 4.58 (1H, ddd, J 9.6, 7.9, 5.4 Hz, CH$\alpha$), 3.65 (3H, s, $CO_2Me$), 3.01 (1H, dd, J 13.9, 5.4 Hz, $CH_AH_BAr$) and 2.85 (1H, dd, J 13.9, 9.6 Hz, $CH_AH_BAr$), m/z (ESI, 60V) 335 ($MH^+$).

INTERMEDIATE 30

N-(2-Chloronicotinoyl)-O-(2,6-dichlorobenzoyl)-L-tyrosine methyl ester

A solution of Intermediate 29 (919 mg, 2.75 mmol) in DMF (10 ml) was added to a suspension of sodium hydride (60% in mineral oil, 3.03 mmol, 121 mg) in DMF (20 ml) at 0°. After 15 min, 2,6-dichlorobenzoyl chloride (414 μl, 2.89 mmol) was added and the mixture stirred for 2 h at room temperature. Water (~5 ml) was added and the solvent removed in vacuo. The residue was dissolved i nEtOAc (150 ml), washed with water (3×50 ml) and brine (50 ml), dried ($Na_2SO_4$) and evaporated in vacuo. Chromatography ($SiO_2$; DCM/MeOH, 98:2) gave the title comound as a white foam (1.10 g, 79%). $\delta$H (DMSO-$d_6$, 300 MHz) 9.12 (1H, d, J 7.6 Hz, CONH), 8.45 (1H, dd, J 4.8, 2.0 Hz, pyrH), 7.69–7.58 (4H, m, pyrH+$Cl_2ArH_3$), 7.46 (1H, dd, J 7.5, 4.9 Hz, pyrH), 7.43 (2H, d, J 8.4 Hz, $ArH_2$), 7.23 (2H, d, J 8.5 Hz, $ArH_2$), 4.73 (1H, m, CH$\alpha$), 3.68 (3H, s, $CO_2Me$), 3.22 (1H, dd, J 13.9, 5.2 Hz, $CH_AH_BAr$) and 3.02 (1H, dd, J 13.9, 10.1 Hz, $CH_AH_BAr$); m/z (ESI, 60V) 507 ($MH^+$).

INTERMEDIATE 31

N-(2-Chloronicotinoyl)-N-methyl-N'-(3,5-dichloro-4-picolyl)-L-4-aminophenylalanine methyl ester 2-Chloronicotinoyl chloride (132 mg, 0.75 mmol) was added to N-methyl-N'-(3,5-dichloroisonicotinyl)-L-4-aminophenylalanine methyl ester [prepared from N-Boc-N'-phthaloyl-4-amino-L-phenylalanine methyl ester and methyl iodide, followed by treatment with hydazine monohydrate and reaction with 3,5-dichloroisonicotinyl chloride with subsequent removal of the Boc group] and NMM (165 μl, 1.5 mmol) in DCM (10 ml). The mixture was stirred for 1 h at room temperature then diluted with DCM (100 ml) and washed with dilute HCl (30 ml), dried ($Na_2SO_4$) and evaporated in vacuo. Chromatography ($SiO_2$; EtOAc/hexane, 10:90) gave the title compound as a colourless gum (380 mg, 97%). $\delta$H (DMSO-$d_6$, 300 MHz, 405K) 10.35 (1H, br s, CONH), 8.67 (2H, s, $Cl_2$pyrH), 8.42 (1H, t, J 3.4 Hz, ClpyrH), 7.55 (2H, br d, J 7.2 Hz, ArH), 7.45–7.15 (4H, v br m, ArH+ClpyrH), 5.3 (1H, v br s, CH$\alpha$), 3.74 (3H, s, $CO_2Me$), 3.4–3.3 (1H, br m, $CH_AH_BAr$), 3.16 (1H, dd, J 14.4, 9.6 Hz, $CH_AH_BAr$) and 2.73 (3H, br s, NMe); m/z (ESI, 60V) 521 ($MH^+$).

INTERMEDIATE 32

[(S-2,5-dimethoxyphenyl)sulphonyl]nicotinoyl-O-(2,6-dichlorobenzyl)-L-tyrosine methyl ester A solution of Intermediate 2 (0.79 g, 1.26 mmol) in DCM (50 ml) was treated with 3-chloroperoxybenzoic acid (2.17 g, 12.6 mmol) and stored at 4° for 48 h. The reaction was partitioned between DCM (20 ml) and NaHCO$_3$ solution (20 ml). The aqueous layer was extracted with DCM (25 ml) and the combined organic layers washed with 10% aqueous Na$_2$SO$_3$ (50 ml), dried (MgSO$_4$) and the solvent removed in vacuo to give a yellow foam that was purified by chromatography (SiO$_2$: EtOAc/hexane 3:1) to give the title compound as a white foam, (0.50 g, 60%). δH (CDCl$_3$) 8.58 (1H, dd, J 4.7, 1.7 Hz, pyr-H), 7.95 (1H, dd, J 7.8, 1.7 Hz, pyr-H), 7.70 (1H, d, J 3.2 Hz, Ar-H), 7.50 (1H, dd, J 7.8, 4.7 Hz, pyr-H), 7.36–7.11 (6H, m, Ar-H), 7.01 (1H, d, J 7.6 Hz, NH), 6.92–6.84 (3H, m, Ar-H), 5.21 (2H, s, CH$_2$O), 5.10 (1H, m, CHα), 3.85 (3H, s, OMe), 3.74 (3H, s, OMe), 3.49 (3H, s, CO$_2$Me) and 3.27 (2H, m, CHCH$_2$Ar). m/z (ESI, 60V) (MH$^+$).

EXAMPLE 1

2-Chloronicotinoyl-O-(2,6-dichlorobenzyl)-L-tyrosine

A solution of Intermediate 1 (0.20 g, 0.41 mmol) in THF (50 ml) and water (5 ml) was treated with lithium hydroxide monohydrate (25 ml, 0.61 mmol. 1.5 equiv.) and stirred at room temperature for 1.5 h. The reaction was acidified to pH1 with 10% hydrochloric acid to give a white precipitate which was isolated by filtration, washed with water (5 ml) and diethyl ether (5 ml) and dried under vacuum to give the title compound as a white powder (0.14 g, 72%). δH (DMSO-d$^6$) 8.93 (1H, d, J 8.1 Hz), 8.45 (1H, dd, J 2.0, 4.8 Hz), 7.66 (1H, dd, J 2.0, 7.5 Hz), 7.56 (2H, m), 7.47 (2H, m), 7.24 (2H, d, J 8.6 Hz), 6.99 (2H, d, J 8.6 Hz), 5.20 (2H, s), 4.60 (1H, d), 3.13 (1H, ABX, J 4.7, 13.9 Hz) and 2.90 (1H, ABX, J 10.0, 13.9 MHz) m/z (ES+, 60V) 479, 481 (MH$^+$).

EXAMPLE 2

2-Thio(S-2,5-dimethoxyphenyl)nicotinoyl-O-(2,6-dichlorobenzyl)-L-tyrosine hydrochloride A solution of Intermediate 2 (0.35 g, 0.56 mmol) in THF (15 ml) and water (7.5 ml) was treated with lithium hydroxide monohydrate (28 mg, 0.67 mmol) and stirred at room temperature for 16 h. The reaction was acidified to pH1 with 10% hydrochloric acid, extracted with DCM (2×30 ml), and the combined organic layers were dried over MgSO$_4$, the solvent removed in vacuo to give a gummy residue, which was purified by chromatography (SiO$_2$; 7.5% MeOH/DCM) to give a gum which was dissolved in acetonitrile (20 ml) and water (20 ml) and lyophylised to give the title compound as a white powder (0.26 g, 71%). δH (DMSO-d$^6$) 8.71 (1H, m), 8.29 (1H, dd, J 1.7, 4.8 Hz), 7.75 (1H, d, J 6.0 Hz), 7.56–6.94 (11H, m), 5.16 (2H, s), 4.56 (1H, m), 3.68 (3H, s), 3.60 (3H, s) and 3.21–1.96 (2H,m). m/z (ES+ 60V) 613, 615 (MH$^+$).

EXAMPLE 3 a) 2-Thio(S-4-picolinyl)nicotinoyl-O-(2,6-dichlorobenzyl)-L-tyrosine

A solution of Intermediate 4 (0.30 g, 0.52 mmol) in THF (7.5 ml) and water (5 ml) was treated with lithium hydroxide monohydrate (33 mg, 0.7 mmol) and stirred at room temperature for 16 h. The pH was adjusted to 6.5–7 with 10% hydrochloric acid to give a yellow precipitate which was isolated by filtration, washed with water and dried in vacuo to give the title compound as a yellow powder (0.28 g, 95%). δH (DMSO-d$^6$) 8.83 (1H, d, J 8.0 Hz), 8.50 (3H, m), 7.75 (1H, d, J 7.6 Hz), 7.56–7.20 (8H, m), 6.95 (2H, d, J 8.5 Hz), 5.17 (2H, s), 4.54 (1H, m), 4.37 (2H, s), 3.12 (1H, m) and 2.97 (1H, m). m/z (ES+, 60 V) 568, 570 (MH$^+$).

The following compounds were prepared in a similar manner by hydrolysis of the corresponding methyl ester. Each ester starting material was obtained either by alkylation of Intermediate 3 or alternative mercaptopyridine using the reagents shown using a similar procedure to that described for Intermediate 4.

b) 2-Thio-S-benzyl-nicotinoyl-(O-2,6-dichlorobenzyl)-L-tyrosine ester from Intermediate 3 and benzyl chloride. δH (DMSO-d$_6$) 8.78 (1H, d, J 8.1 Hz, pyr-H), 8.54 (1H, dd, J 4.8, 1. Hz, pyr-H), 7.69 (1H, dd, J 7.7,1.7 Hz, pyr-H), 7.68–7.17 (11H, m, Ar-H), 6.94 (2H, d, J 8.6, Ar-H), 5.16 (2H, s, CH$_2$O), 4.53 (1H, m CHα), 4.34 (2H, s, CH$_2$Ar), 3.10 (1H, dd, J 13.9, 4.6 Hz, CHC$\underline{H}_A$H$_B$Ar), 2.94 (1H, dd, J 13.9, 10.2 Hz, CHCH$_A\underline{H}_B$Ar); m/z (ESI, 60V) 567 (MH$^+$).

c) 2-Thio-(S-4-Methylphenyl)-nicotinoyl-(O-2,6-dichlorobenzyl-L-tyrosine ester from Intermediate 3 and 4-methylbenzyl chloride. δH (DMSO-d$_6$) 8.87 (1H, d, J 8.1 Hz, pyr-H), 8.31 (1H, dd, J 4.7,1.8 Hz, pyr-H), 7.70 (1H, dd, J 7.6, 1.7 Hz, pyr-H), 7.54 (2H, m, Ar-H), 7.45 (1H, m, Ar-H), 7.32–7.17 (7H, m, Ar-H), 6.98 (2H, d, J 8.6 Hz, Ar-H), 5.17 (2H, s, CH$_2$O), 4.58 (1H, m, CHα), 3.16 (1H, dd, J 14.6, 14.0 Hz, CHC$\underline{H}_A$H$_B$Ar), 2.98 (1H, dd, J 14.0, 10.1 Hz, CHCH$_A\underline{H}_B$Ar) and 2.32 (3H, s, Me); m/z (ESI, 60V) 569 (MH$^+$).

d) 2-Thio-S-(3-picolyl)-nicotinoyl-(O-2,6-dichlorobenzyl)-L-tyrosine ester from Intermediate 3 and 3-picolyl chloride. δH (DMSO-d$_6$) 9.04–8.54 (5H, m, Ar-H), 7.95–7.84 (2H, m, Ar-H), 7.56–7.43 (3H, m, Ar-H), 6.96 (2H, d, J 8.3 Hz, Ar-H), 5.17 (2H, s, CH$_2$O), 4.55 (1H, m, CHα), 4.48 (2H, s, CH$_2$pyr), 3.05 (2H, m, CHC$\underline{H}_2$Ar); m/z (ESI, 60V) 569 (MH$^+$).

e) N-[2-thio(S-3-picolinyl)nicotinoyl]-O-,2,6-dichlorobenzyl-L-tyrosine ester from Intermediate 3 and 3-picoyl chloride using DBU as base. δH (DMSO-d$_6$) 8.8 (1H, br d), 8.57 (1H, m), 8.50 (1H, m), 7.72 (2H, m), 7.55 (1H, d), 7.5–7.4 (2H, m), 7.3–7.15 (4H, m), 6.95 (2H, d), 5.15 (2H, s), 4.55–4.45 (3H, m), 3.2–3.1 (1H, m), 3.0–2.9 (1H, m); m/z (ESI, 60V) 568 (MH$^+$).

f) N-2-Thio(S-4-butanoate)nicotinoyl]-(O-2,6-dichlorobenzyl)-L-tyrosine ester from Intermediate 3 and methyl-4-chlorobutyrate using K$_2$CO$_3$ as base. δH (DMSO-d$_6$) 8.76 (1H, d, J 8.1 Hz), 8.49 (1H, dd, J 4.8, 1.7 Hz), 7.61 (1H, dd, J 7.7, 1.7 Hz), 7.55 (2H, d, J 8.9 Hz), 7.45 (1H, m), 7.23 (2H, d, J 8.5 Hz), 7.2 (1H, m), 6.96 (2H, d, J 8.5 Hz), 5.18 (2H, s), 4.53 (1H, m), 3.17–2.87 (4H, m), 2.40–2.30 (2H, t, J 7.3 Hz), 1.83 (2H, m); m/z (ESI, 60V) 563 (MH$^+$).

g) (N'-3,5-Dichloroisonicotinoyl)-N-{([3-pyridinylmethyl]thio)isonicotinoyl}-L-4-aminophenylalanine ester from 2-mercaptoisonicotinoyl-(N'-3,5-dichloroisonicotinoyl)-L-4-aminophenylalanine and 3-picolyl chloride. δH (DMSO-d$_6$) 10.86 (1H, s, CO$_2$H), 8.92–8.75 (3H, m, ArH), 8.68–8.52 (2H, m), 8.39 (1H, br s), 7.75 (2H, t, J 7.5 Hz), 7.56 (2H, d, J 6.3 Hz), 7.39–7.18 (4H, m), 4.60–4.47 (1H, m, CH) and 3.25–2.92 (2H, m, CH$_2$); m/z (ESI, 60V) 582 (MH$^+$).

EXAMPLE 4 a) 2-Thio(S-2,5-dimethoxyphenyl)nicotinoyl-(N-2,6-dichlorobenzoyl)-L-4-aminophenylalanine A solution of Intermediate 6 (0.44 g, 0.69 mmol) in THF (7.5 ml) and water (5 ml) was treated with lithium hydroxide monohydrate (43 mg, 1.0 mmol) and stirred at room temperature for 16 h, then acidified to pH1 with 10% hydrochloric acid. The mixture was extracted with DCM (2×30 ml) and the solvent evaporated in vacuo to give an off-white solid that was triturated with boiling MeOH to give the title compound as a white solid (210 mg, 49%). δH (DMSO-d$^6$) 11.18 (1H, br s, CO$_2$H), 10.66 (1H, s, NH), 8.89 (1H, d, J 8.0 Hz) 8.30 (1H, dd, J 1.6, 4.7 Hz), 7.77 (1H, dd, J 1.6, 7.6 Hz), 7.62–7.45 (5H, m), 7.32 (2H, d, J 8.5 Hz), 7.17 (1H, dd, J 4.8, 7.6 Hz), 6.96 (3H, m), 4.62 (1H, m), 3.70 (3H, s), 3.60 (3H, s) and 3.20–3.00 (2H, m). m/z (ES+) 626,628 (MH$^+$).

The following compounds were prepared in a similar manner to the compound of Example 4a) by hydrolysis of the corresponding methyl ester. Each ester was obtained by coupling the starting materials shown according to the method described for Intermediate 6:

a) 2-Thio(S-2,5-dimethoxyphenyl)nicotinoyl-(N-2,6-dichlorobenzoyl)-L-4-aminophenylalanine from (N-2,6-dichlorobenzoyl)-L-4-aminophenylalanine methyl ester and 3,5-dichloropyridyl-4-carbonyl chloride. δH (DMSO-d$_6$) 8.64 (2H, s), 7.60–7.46 (5H, m), 7.24 (2H, d, J 8.5 Hz), 4.78–4.65 (1H, m), 3.22–2.85 (2H, m); δH m/z (ESI, 60V) 528 (MH$^+$).

c) (N'-2,4-Dimethylnicotinoyl)-(N-2,6-dichlorobenzoyl)-L-4-aminophenylalanine from (N-2,6-dichlorobenzoyl)-L-4-aminophenylalanine methyl ester and 2,4-dimethylpyridyl-4-carbonyl chloride. δH (DMSO-d$_6$) 8.39 (1H, br d), 8.23 (1H, d, J 5.0 Hz), 7.59–7.45 (6H, m), 7.26 (2H, d, J 8.4 Hz), 7.01 (1H, d, J 5.1 Hz), 4.65–4.52 (1H, m), 3.26–3.18 (1H, m), 2.95–2.84 (1H, m), 2.17 (3H, s), 2.01 (3H, s); m/z (ESI, 60V) 486 (MH$^+$).

d) N-(2,6-Dichloroisonicotinoyl)-O-(2,6-dichlorobenzyl)-L-tyrosine from O-(2,6-dichlorobenzyl)-L-tyrosine methyl ester hydrochloride and 2,6-dichloropyridyl-4-carbonyl chloride. δH (DMSO-d$_6$) 9.2 (1H, d), 7.81 (2H, s), 7.5–7.3 (3H,m), 7.21 (2H, d, J 8.5 Hz), 6.93 (2H, d, J 8.5 Hz), 5.15 (2H, s), 4.65 (1H, m), 3.28–3.15 (1H, m), 3.05–2.95 (1H, m); m/z (ESI, 60V) 513 (MH$^+$).

e) N'-(2-nicotinoyl)-O-(2,6-dichlorobenzyl)-L-tyrosine from O-(2,6-dichlorobenzyl)-L-tyrosine methyl ester hydrochloride and nicotinoyl chloride using triethylamine as base. δH (DMSO-d$_6$) 9.0–8.85 (2H, m), 8.7 (1H,m), 8.14 (1H, m), 7.55–7.41 (4H, m), 7.24 (2H, d, J 8.6 Hz), 6.95 (2h, d, J 8.6 Hz), 5.16 (2H, s), 4.59 (1H, m), 3.17–3.12 (1H, m), 3.04–2.96 (1H,m); m/z (ESI, 60V) 445 (MH$^+$).

f) N-(3,5-Dichloro-4-picolyl)-N'-(3,5-dichloro-4-picolyl)-L-4-aminophenylalanine from (N-3,5-dichloro-4-picolyl)-L-4-aminophenylalanine methyl ester and 3,5-dichlorophridyl-4-carbonyl chloride. δH (DMSO-d$_6$, 300 MHz) 9.26 (1H, d, J 8.3 Hz), 8.79 (2H, s), 8.65 (2H, s), 7.57 (2H, d, J 8.4 Hz), 7.30 (2H, d, J 8.4 Hz), 4.70 (1H,m), 3.15 (1H, dd, J 14.1, 5.2 Hz) and 2.93 (1H, dd, J 14.0, 9.3 Hz); m/z (ESI, 160V) 527 (MH$^+$).

g) N-(2-Chloronicotinoyl)-N'-(3,5-dichloro-4-picolyl)-L-4-aminophenylalanine from (N-3,5-dichloro-4-picolyl)-L-4-aminophenylalanine methyl ester and 2-chloro-nicotinoyl chloride. δH (DMSO-d$_6$, 300 MHz) 12.85 (1H, br s), 10.88 (1H, s), 8.97 (1H, d, J 8.1 Hz), 8.79 (2H, s), 8.46 (1H, dd, J 4.8, 1.8 Hz), 7.70 (1H, dd, J 7.5, 1.8 Hz), 7.59 (2H, d, J 8.4 Hz), 7.48 (1H, dd, J 7.5, 4.8 Hz), 7.30 (2H, d, J 8.4 Hz), 4.63 (1H, m), 3.16 (1H, dd, J 13.9, 4.7 Hz) and 2.95 (1H, dd, J 13.8, 9.8 Hz) m/z (ESI, 160V) 493 (MH$^+$).

EXAMPLE 5 a) O-(2,6-dichlorobenzyl)-N-(4-acetyl-1,2,5-trimethyl-3-pyrroyl)-L-tyrosine

Intermediate 7 (360 mg, 0.68 mmol) was treated with LiOH.H$_2$O (34 mg, 0.81 mmol) in dioxane (6 ml), water (6 ml) and MeOH (4 ml) at room temperature for 2 h. The solvent was removed in vacuo and the obtained residue taken up in water. The pH was made acidic by addition of a few drops of acetic acid and the obtained precipitate filtered off with water washing affording the title compound as a white amorphous powder (245 mg, 70%). δH (d$^6$-DMSO) 8.37 (1H, d, J 8.2 Hz, NH), 7.57–7.43 (3H, m's, aryl-H), 7.23 (2H, d, J 8.6 Hz, aryl-H), 6.95 (2H, d, J 87.6 Hz, aryl-H), 5.18 (2H, br s, CH$_2$—O), 4.62 (1H, m, αtyr-H), 3.33 (3H, s, MeN), 3.13 (1H, dd, J 4.1, 13.8 Hz, CH$_A$H$_B$Ar), 2.32 (3H, s, MeCO), 2.01 (3H, s, pyrrole-Me) and 1.92 (3H, s, pyrrole-Me). m/z (ES+, 60V), 517 (MH$_+$, 100), 519 (MH$^+$, 70).

The following compounds were prepared in a similar manner to the compound of Example 5a) by hydrolysis of the corresponding methyl ester. Each ester was obtained by coupling the starting materials shown according to the method described for Intermediate 7:

b) O-(2,6-dichlorobenzyl)-N-(4-acetyl-3,5-dimethyl-2-pyrroyl)-L-tyrosine from O-(2,6-dichlorobenzyl)-L-tyrosine methyl ester hydrochloride and 3,5-dimethyl-4-acetylpyrrole-2-carboxylic acid. Freeze drying afforded the title compound as a light cream amorphous solid (550 mg). δH (DMSO-d$_6$) 11.56, (1H, s), 7.61 (1H, d, J 7.8 Hz), 7.51 (2H, d, J 8.0 Hz), 7.41 (1H, t, J 8.0 Hz), 7.21 (2H, d, J 85 Hz), 6.96 (2H, d, J 8.5 Hz), 5.16 (2H, s), 4.69–4.55 (1H, m), 3.12 (1H, dd, J 13.7, 4.7 Hz), 2.99 (1H, dd, J 13.7, 9.1 Hz), 2.43 (3H, s), 2.38 (3H, s), 2.31 (3H, s); m/z (ESI, 60V) 503 (MH$^+$).

c) O-(2,6-dichlorobenzyl)-N-(4-acetyl-2,5-dimethyl-3-pyrrolyl)-L-tyrosine from O-(2,6-dichlorobenzyl)-L-tyrosine methyl ester hydrochloride and 2,5-dimethyl-4-acetyl-pyrrole-3-carboxylic acid. Freeze drying afforded the title compound as a white amorphous solid (203 mg). δH (DMSO-d$_6$) 11.2 (1H, s), 8.83 (1H, d, J 8.0 Hz), 7.56 (2H, app.d. J 8.0 Hz), 7.45 (1H, app.t, J 8.0 Hz), 7.21 (2H, d, J 8.5 Hz), 6.95 (2H, d, J 8.5 Hz), 5.17 (2H, s), 4.61–4.52 (1H, m), 3.11 (1H, dd, J 13.8, 4.3 Hz), 2.86 (1H, dd, J 13.8, 10.4 Hz), 2.31 (3H, s), 2.08 (3H, s), 2.07 (3H, s); m/z (ESI, 60V) 503 and 505 (MH$^+$).

d) O-(2,6-dichlorobenzyl)-N-(1-methyl-2-indolyl)-L-tyrosine from O-(2,6-dichlorobenzyl)-L-tyrosine methyl ester hydrochloride and 1-methylindole-2-carboxylic acid. Freeze drying afforded the title compound as a white amorphous solid (220 mg). δH (DMSO-$d_6$) 11.7 (1H, br s), 8.66 (1H, d, J 8.3 Hz), 7.65 (1H, d, J 7.9 Hz), 7.53 (2H, app.d, J 8/1 Hz), 7.26 (1H, obscured m), 7.09 (2H, app.t, J 7.5 Hz), 6.96 (2H, d, J 8.5 Hz), 5.16 (2H, s), 4.64–4.54 (1H, m), 3.89 (3H, s), 3.16 (1H, dd, J 13.8, 4.3 Hz) and 3.00 (1H, dd, J 13.8, 10.4 Hz); m/z (ESI, 60V) 497 and 499 (MH$^+$).

e) O-(2,6-dichlorobenzyl)-N-[2-(4-chlorophenyl)-3-(trifluoromethyl)-4-pyrazoyl]-L-tyrosine from O-(2,6-dichlorobenzyl)-L-tyrosine methyl ester hydrochloride and 2-(4-chlorophenyl)-3-(trifluoromethyl)-pyrazole-4-carboxylic acid. The title compound was isolated as an off-white solid (220 mg). δH (DMSO-$d_6$) 11.17 (1H, br s), 8.82 (1H, d, J 8.2 Hz), 8.08 (1H, s), 7.65 (2H, d, J 8.1 Hz), 7.54 (4H, app. d, J 8.1 Hz), 7.45 (1H, app. t, J 8.0 Hz), 7.24 (2H, d, J 8.3 Hz), 6.98 (2H, d, J 8.3 Hz), 5.18 (2H, s), 4.61–4.51 (1H, m), 3.17 (1H, dd, J 13.8, 4.5 Hz), and 2.94 (1H, dd, J 13.8, 9.0 Hz); m/z (ESI, 60V) 527 and 529 (MH$^+$).

f) O-(2,6-dichlorobenzyl)-N-(2-phenyl-4-thiazoyl)-L-tyrosine from O-(2,6-dichlorobenzyl)-L-tyrosine methyl ester hydrochloride and 2-phenyl-thiazole-4-carboxylic acid. Freeze-drying afforded the title compound as a pale yellow amorphous solid (340 mg). δH (DMSO-$d_6$) 11.2 (1H, br s), 8.40 (1H, d, J 8.1 Hz), 8.31 (1H, s), 8.05–8.02 (2H, m), 7.55–7.51 (5H, m), 7.46–7.40 (1H, m), 7.23 (2H, d, J 8.0 Hz), 6.97 (2H, d, J 7.8 Hz), 5.16 (2H, s), 4.71–4.64 (1H, m), 3.18 (2H, app. d, J 6.6 Hz); m/z (ESI, 60V) 527 and 529 (MH$^+$).

g) (N'-1-Methyl-5-nitropyrazolyl)-(N-2,6-dichlorobenzoyl)-L-4-aminophenyalanine from (N-2,6-dichlorobenzoyl)-L-4-aminophenylalanine methyl ester with N-methyl-5-nitropyrazole-4-carboxylic acid. δH (DMSO-$d_6$) 10.64-(1H, s), 8.68 (1H, br d), 7.80 91H, s), 7.64–7.48 (6H, m), 7.19 (2H, d, J 8.5 Hz), 4.59–4.49 (1H, m), 4.05 (3H, s), 3.18–2.9 (2H, m); m/z (ESI, 60V) 506 (MH$^+$).

h) N-(2-Methylnicotinoyl)-O-(2,6-dichlorobenzyl)-L-tyrosine from O-(2,6-dichlorobenzyl)-L-tyrosine methyl ester hydrochloride and 2-methylnicotinic acid. δH (DMSO-$d_6$) 8.73 (1H, br d), 8.48 (1H, m), 7.7–7.46 (4H, m), 7.4–7.23 (3H, m), 7.00 (2H, d, J 8.4 Hz), 5.2) (2H, s), 4.60 91H, m), 3.27–3.12 (1H, m), 3.0–2.82 (1H, m); m/z (ESI, 60V) 509 (MH$^+$).

i) (N'-2-Chloronicotinoyl)-(N-benzoyl)-L-4-aminophenylalanine from (N-benzoyl)-L-4-aminophenylalanine methyl ester and 2-chloronicotinic acid. δH (DMSO-$d_6$) 10.19 (1H, s), 8.96 (1H, d, J 8.2 Hz), 8.46 (1H, dd, J 4.8, 1.9 Hz), 7.96 (2H, dd, J 6.7, 1.7H), 7.75–7.65 (3H, m), 7.62–7.45 (4H, m), 7.25 (2H, d, J 8.5 Hz), 4.6 (1H, m), 3.2–3.12 (1H, m), 3.0–2.89 (1H, m), m/z (ESI, 60V) 424 (MH$^+$).

j) N'-(Quinoline-4-carbonyl)-O-(2,6-dichlorobenzyl)-L-tyrosine from O-(2,6-dichlorobenzyl)-L-tyrosine methyl ester hydrochloride and 4-quinoline carboxylic acid. δH (DMSO-$d_6$) 9.0 (1H, d), 8.94 (1H, d, J 4.3), 8.06 (1H, d, J 8.2 Hz), 7.79 (2H, m), 7.62–7.42 (4H, m), 7.34 (1H, d, J 4.3 Hz), 7.34 (2H, d, J 8.7 Hz), 7.00 (2H, d, J 8.7 Hz), 5.22 (2H, s), 4.72 (1H, m), 3.29–3.19 (1H, m), 3.0–2.88 (1H, m); m/z (ESI, 60V) 495 (MH$^+$).

k) N'-(2-Phenoxynicotinoyl)-O-(2,6-dichlorobenzyl)-L-tyrosine from O-(2,6-dichlorobenzyl)-L-tyrosine methyl ester hydrochloride and 2-phenoxynicotinic acid. δH (DMSO-$d_6$) 8.55 (1H, d), 8.18 (2H, m), 7.6–7.4 (5H, m), 7.3–7.15 (6H, m), 6.71 (2H, d), 5.1 (2H, s), 4.65 (1H, m), 3.22–3.0 (2H, m); m/z (ESI, 60V) 537 (MH$^+$).

l) N-(Pyridine-2-carbonyl)-O-(2,6-dichlorobenzyl)-L-tyrosine from O-(2,6-dichlorobenzyl)-L-tyrosine methyl ester hydrochloride and 2-picolinic acid. δH (DMSO-$d_6$) 8.8–8.6 (2H, m), 8.0 (2H, m), 7.7–7.4 (4H, m), 7.14 (2H, d, J 8.7 Hz), 6.92 (2H, d, J 8.7 Hz), 5.15 (2H, s), 4.72 (1H, m), 3.17 (2H, m); m/z (ESI, 60V) 445 (MH$^+$).

m) N-(Pyridine-4-carbonyl)-O-(2,6-dichlorobenzyl)-L-tyrosine from O-(2,6-dichlorobenzyl)-L-tyrosine methyl ester hydrochloride and isonicotinic acid. δH (DMSO-$d_6$) 8.68 (2H, dd, J 4.5, 1.6 Hz), 8.4 (1H, d, J 7.2 Hz), 7.63 (2H, dd, J 4.5, 1.6 Hz), 7.6–7.4 (3H, m), 7.15 (2H, d, J 8.6 Hz), 6.87 (2H, d, J 8.6 Hz), 5.14 (2H, s), 4.31 (1H, m), 3.2–2.96 (2H, m); m/z (ESI, 60V) 445 (MH$^+$).

n) N-(2-Hydroxynicotinoyl)-O-(2,6-dichlorobenzyl)-L-tyrosine)

from O-(2,6-dichlorobenzyl)-L-tyrosine methyl ester hydrochloride and 2-hydroxynicotinic acid. δH (DMSO-$d_6$) 10.15 (1H, d, J 7.4 Hz), 8.31 (1H, dd, J 7.1, 2.0 Hz), 7.71 (1H, br s), 7.65–7.45 (3H, m), 7.16 (2H, d, J 8.4 Hz), 6.97 (2H, d, J 8.4 Hz), 6.46 (1H, t, J 6.8 Hz), 5.17 (2H, s), 4.68 (1H, m), 3.2–3.0 (2H, m); m/z (ESI, 60V) 461 (MH$^+$).

o) (N'-2-Aminonicotinoyl)-(N-2,6-dichlorobenzoyl)-L-4-amino phenylalanine from (N-2,6-dichlorobenzoyl)-L-4-aminophenylalanine methyl ester and 2-aminonicotinic acid. δH (DMSO-$d_6$) 10.64 (1H, s), 8.55 (1H, d), 8.06 (1H, m), 7.8 (1H, d), 7.7–7.4 (4H, m), 7.28 (2H, d, J 8.5 Hz), 6.9 (2H, br s), 6.5 (1H, m), 4.52 (1H, m), 3.2–2.9 (2H, m); m/z (ESI, 60V) 473 (MH$^+$).

p) (N'-2-Hydroxynicotinoyl)-(N-3,5-dichloroisonicotinoyl)-L-4-aminophenylalanine from (N-3,5-dichloroisonicotinoyl)-L-4-aminophenylalanine methyl ester and 2-hydroxynicotinic acid. δH (DMSO-$d_6$) 10.14 (1H, d, J 7.6 Hz), 8.78 (2H, s), 8.31 (1H, dd, J 7.2, 2.2 Hz), 7.70 (1H, br m), 7.57 (2H, d, J 8.5 Hz), 7.20 (2H, d, J 8.5 Hz), 6.46 (1H, m), 4.69 (1H, m), 3.20–2.95 (2H, m); m/z (ESI, 60V) 475 (MH$^+$).

q) (N'-2-Methylnicotinoyl)-(N-3,5-dichloroisonicotinoyl)-L-4-aminophenylalanine from (N-3,5-dichloroisonicotinoyl)-L-4-aminophenylalanine and 2-methylnicotinic acid. δH (DMSO-$d_6$) 8.78 (2H, s), 8.60 (1H, br d), 8.48 (1H, dd, J 4.8, 1.6 Hz), 7.7–7.5 (3H, m), 7.4–7.2 (3H, m), 4.5 (1H,), 3.3–2.85 (2H, m), 2.34 (3H, s); m/z (ESI, 60V) 473 (MH$^+$).

r) (N'-2,6-Dichlorobenzoyl)-(N-2-phenoxynicotinoyl)-L-4-aminophenylalanine from (N-2,6-dichlorobenzoyl)-L-4-aminophenylalanine methyl ester and 2-phenoxynicotinic acid. δH (DMSO-d$_6$) 10.61 (1H, s), 8.56 (1H, d, J 7.5 Hz), 8.22–8.17 (2H, m), 7.59–7.39 (8H, m), 7.27–7.11 (7H, m), 4.72–4.64 (1H, m, CH), 3.16 (1H, dd, J 13.7, 4.9 Hz, CH$_A$H$_B$) and 3.06 (1H, dd, J 13.7, 7.8 Hz, CH$_A$H$_B$); m/z (ESI, 60V) 550 (MH$^+$).

s) (N'3,5-Dichloroisonicotinoyl)-(N-2-phenoxynicotinoyl)-L-4-aminophenylalanine from (N-3,5-dichloroisonicotinoyl)-L-4-aminophenylalanine methyl ester and 2-phenoxynicotinic acid. δH (DMSO-d$_6$) 10.79 (1H, s), 8.78 (2H, s, ArH), 8.57 (1H, d, J 7.6 Hz), 8.25–8.13 (2H, m), 7.46–7.35 (4H, m), 7.29–7.05 (6H, m), 4.73–4.62 (1H, m, CH), 3.17 (1H, dd, J 13.7, 4.7 Hz, CH$_A$H$_B$) and 3.09 (1H, dd, J 13.7, 7.8 Hz, CH$_A$H$_B$); m/z (ESI, 60V) 551 (MH$^+$).

t) N-(4-Acetyl-1,2,5-trimethyl-1H-pyrrole-3-carbonyl)-N'-(3,5-dichloro-4-picolyl)-L-4-aminophenylalanine from (N-3,5-dichloro-4-picolyl)-L-4-aminophenylalanine methyl ester and 4-acetyl-1,2,5-trimethyl-1H-pyrrole-3-carboxylic acid. δH (DMSO-d$_6$, 300MHz) 400K) 12.72 (1H, br s), 10.83 (1H, s), 8.80 (2H, s), 8.42 (1H, d, J 8.4 Hz), 7.54 (2H, d, J 8.5 Hz), 7.30 (2H, d, J 8.4 Hz), 4.66 (1H, m), 3.34 (3H, s), 3.16 (1H, dd, J 13.8, 4.3 Hz), 2.89 (1H, dd, J 13.8, 11.0 Hz), 2.32 (3H, s), 2.05 (3H, s), and 1.90 (3H, s); m/z (ESI, 60V) 531 (MH$^+$).

u) N-(4-Carboxy)nicotinoyl)-N'-(3,5-dichloro-4-picolyl)-L-4-aminophenylalanine from (N-3,5-dichloro-4-picolyl)-L-4-aminophenylalanine methyl ester and 4-(methoxycarbonyl)nicotinic acid. δH (DMSO-d$_6$, 300MHz) 10.98 (1H, s), 9.01 (1H, d, J 8.0 Hz), 8.77 (2H, s), 8.63 (1H, s), 7.66 (1H, s, J 5.1 Hz), 7.59 (2H, d, J 8.5 Hz), 7.32 (2H, d, J 8.5 Hz), 4.63 (1H, m), 3.14 (1H, dd, J 13.9, 5.4 Hz) and 3.03 (1H, dd, J 13.9, 8.8 Hz); m/z (ESI, 160V) 503 (MH$^+$).

v) (2-Acetyl-3-thienyl)carbonyl-(N-3,5-dichloro-4-picolinyl)-4-aminophenylalanine from (N-3,5-dichloro-4-picolyl)-L-4-aminophenylalanine methyl ester and 2-acetyl-thiophene-3-carboxylic acid. δH (DMSO-d$_6$) 9.17 (1H, d, J 8.2 Hz, NH), 8.77 (2H, s, pyr-H), 7.99 (1H, d, J 5.1 Hz, thiophene H-5), 7.57 (2H, ABd, J 8.5 Hz, Ar-H), 7.31 (2H, ABd, 2H, J 8.5 Hz, Ar-H), 7.07 (1H, d, J 5.1 Hz, thiophene H-4), 5.38 (1H, m, CHα), 3.18 (1H, dd, J 13.8, 4.6 Hz, CHCH$_A$H$_B$Ar), 2.93 (1H, dd, J 13.8, 10.3 Hz, CHCH$_A$H$_B$Ar) and 2.26 (3H, s, COMe); m/z (ESI, 60V) 506 (MH$^+$).

EXAMPLE 6 a) 2-Chloronicotinoyl-(N-2,6-dichlorobenzoyl)-L-4-aminophenylalanine

Lithium hydroxide monohydrate (109 mg, 2.5 mmol) was added to a solution of Intermediate 8 (450 mg, 1 mmol) in a mixture of THF (10 ml) and water (10 ml). The mixture was stirred for 2 h at room temperature, then the THF was evaporated in vacuo. The aqueous residue was neutralised (1M hydrochloric acid), and the precipitate isolated by filtration, washed with water and dried to give the title compound (300 mg, 61%). δH (DMSO-d$^6$, 400K) 8.90 (1H, d, J 9.1 Hzm 1NH), 8.48 (1H, m, Py H), 7.69 (1H, m, Py H), 7.64–7.45 (7H, m, 4ArH, 1 NH, 1 PyH), 7.29 (2H, d, J 8.3 Hz, 2 ArH), 4.66–4.53 (1H, m, CHαtyr), 3.18 (1H, dd, J 14, 5.2 Hz CH$_A$H$_B$Ar), and 2.91 (1H, dd, J 9.6, 14 Hz, CH$_A$H$_B$Ar). m/z (ESI, 60V) 491 (MH$^+$).

The following compounds were prepared in a similar manner:

b) N-(2-Chloronicotinoyl)-O-(2,6-dichlorobenzoyl)-L-tyrosine from Intermediate 30 to give the title compound as a white solid. δH (DMSO-d$_6$, 300MHz), 12.91 (1H, br s, CO$_2$H), 8.98 (1H, d, H 8.3 Hz, CONH), 8.44 (1H, dd, J 4.8, 1.9 Hz, PyH), 7.69–7.58 (4H, m, Cl$_2$ArH$_3$+PyH), 7.45 (1H, dd, J 7.5, 4.9 Hz, PyH), 7.43 (2H, d, J 8.7 Hz, ArH), 7.22 (2H, d, J 8.5 Hz, ArH), 4.67 (1H, ddd, J 10.0, 8.2, 4.7 Hz, CHα), 3.24 (1H, dd, J 14.0, 4.0 Hz, CH$_A$H$_B$Ar) and 2.99 (1H, dd, J 13.9, 10.2 Hz, CH$_A$H$_B$Ar); m/z (ESI, 60V) 493 (MH$^+$).

c) N-(2-Chloronicotinoyl)-N-methyl-N'-(3,5-dichloro-4-picolyl)-L-4-aminophenylalanine from Intermediate 31 to give the title compound as a white solid δH (DMSO-d$_6$, 300MHz, 405K) 10.36 (1H, br s, CONH), 8.57 (2H, s, Cl$_2$PyH), 8.42–8.39 (1H, m, ClPyH), 7.54–7.15 (6H, br m, 4×ArH+2×ClPyH), 5.30 (1H, v br s, CHα), 3.4–2.6 (5H, br m, NMe+CHCH$_2$Ar) (Acid proton not observed at 405K, at 300K δH 13.06 (1H, br s, CO$_2$H)); m/z (ESI, 70V) 507 (MH$^+$).

d) [(S-2,5-dimethoxyphenyl)sulphonyl]nicotinoyl-O-(2,6-dichlorobenzyl)-L-tyrosine from Intermediate 32 δH (DMSO-d$_6$) 8.57 (2H, m, pyrH, NH), 7.83 (1H, d, J 7.8 Hz, pyr-H), 7.69 (1H, dd, J 7.8, 4.7 Hz, pyr-H), 7.55 (4H, m, Ar-H), 7.28–7.22 (3H, m, Ar-H), 7.07 (1H, d, J 9.1 Hz, Ar-H), 6.95 (2H, d, J 8.5 Hz, Ar-H), 5.18 (1H, s, CH$_2$O), 4.55 (1H, m, CHα), 3.81 (3H, s, OMe), 3.40 (3H, s, OMe) and 3.07 (2H, m, CHCH$_2$Ar). m/z (ESI, 30V) 645 (MH$^+$).

e) 2-{[(2-Chloro-3-pyridinyl)carbonyl]amino}-3-(4-{(2,6-dichloroanilino)carbonyl}phenyl)propanoic acid from Intermediate 15 to give the title compound as an off white solid δH (DMSO-d$_6$, 300K) 11.06 (1H, br s), 10.23 (1H, br s), 9.00 (1H, d, J 7.8 Hz), 8.46 (1H, br d), 7.95 (2H, d, J 7.4 Hz), 7.69 (1H, d, J 7.1 Hz), 7.59 (2H, d, J 8.0 Hz), 7.50–7.36 (3H, m), 4.71 (1H, br), 3.26 (1H) and 3.06 (1H, dd, J 13.8, 10.0 Hz); m/z (ESI, 60V) 492 (MH$^+$).

f) 2-{[(2-Chloro-3-pyridinyl)carbonyl]amino}-3-(4-{[(3,5-dichloro-4-pyridinyl)amino]carbonyl}phenyl propionic acid from the corresponding intermediate ester prepared in a similar way to Intermediate 15 to give title compounds as an offwhite solid. δH (DMSO-d$_6$, 300MHz), 12.92 (1H, br s), 10.57 (1H, s), 9.00 (1H, d, J 8.2 Hz), 8.75 (2H, s), 8.45 (1H, dd, J 4.7, 1.7 Hz), 7.96 (2H, d, J 8.15 Hz), 7.69 (1H, d, J 7.3, 1.7 Hz), 7.49 (2H, d, J 8.0 Hz), 7.48 (1H, 4.71 (1H, br m), 3.28 (1H, dd, J 13.9, 4.7 Hz) and 3.06 (1H, dd, J 13.9, 10.0 Hz); m/z (ESI, 60V) 483 (MH$^+$).

EXAMPLE 7

2-Thio(S-acetic acid)nicotinoyl-O-(2,6-dichlorobenzyl)-L-tyrosine

Lithium hydroxide monohydrate (75 mg, 1.8 mmol) was added to a solution of Intermediate 9 (360 mg, 0.6 mmol) in a mixture of THF (13 ml) and water (10 ml). The mixture was stirred for 2 hr at room temperature, then the THF was evaporated in vacuo. The aqueous residue was neutralised (1M hyrochloric acid), and the precipitate isolated by filtration, washed with water and dried to give the title compound (200 mg, 58%). δH (DMSO-$d_6$), 400K), 8.5–8.35 (2H, m, pyrH, 1NH), 7.71 (1H, dd, J 1.7, 7.6, pyrH), 7.57 (2H, d, J 8.9, 2ArH), 7.45 (1H, m, 1ArH), 7.22 (2H, d, J 8.5, 2ArH), 7.18 (1H, m, 1pyrH), 6.97 (2H, d, J 8.5, 2ArH), 5.18 (2H, s, OCH$_2$Ar), 4.43 (1H, m, CHαtyr), 3.82 (2H, s, SC$\underline{H}_2$CO$_2$H), 2.94–3.23 (2H, m, CH$_2$Ar); m/z (ESI, GOU) 535 (MH$^+$).

EXAMPLE 8

2-Thio(S-methyl)nicotinoyl-O-(2,6-dichlorobenzyl)-L-tyrosine

Lithium hydroxide monohydrate (140 mg, 3.3 mmol) was added to a solution of Intermediate 10 (1.4 gm, 2.7 mmol) in a mixture of THF (10 ml) and water (10 ml). The mixture was stirred for 2 hr at room temperature then the THF was evaporated in vacuo. The aqueous residue was neutralised (1M hydrochloric acid), and the precipitate isolated by filtration, washed with water and dried to give the title compound (1.1 gm, 81%). δH (DMSO-$d_6$, 400K) 8.73 (1H, d, J 8.1, NH), 8.52 (1H, dd, J 1.7, 4.8, 1pyrH), 7.67 (1H, dd, J 1.7, 7.6, 1pyrH), 7.55 (2H, d, J 8.9, 2ArH), 7.45 (1H, dd, J 2.3, 8.9, 1ArH), 7.24 (2H, d, J 8.6, 2ArH), 7.16 (1H, m, 1pyrH), 6.99 (2H, d, J 8.6, 2ArH), 5.18 (2H, s, OCH$_2$Ar), 4.55 (1H, m, CH$_2$tyr), 3.16–2.95 (2H, m, CH$_2$Ar) and 2.38 (3H, s, SCH$_3$); m/z (ESI, GOU) 491 (MH$^+$).

EXAMPLE 9

(N-2-Chloronicotinoyl)-4-[(E)-2-(2,6-dichlorophenyl)ethenyl]phenylalanine

To a solution of Intermediate 28 (1.0 g, 1.99 mmol) in THF (5 ml) and water (5 ml) was added lithium hydroxide monohydrate (88 mg 2.09 mmol). The reaction mixture was stirred for 1 h. The THF was then removed in vacuo and the remaining aqueous solution acidified to pH6 with 1M hydrochloric acid. The resulting precipitate was collected and washed with water and ether and finally freeze dried. The resulting compound contained an impurity so a small amount was purified by preparavie HPLC (98 mg). δH (DMSO-$d_6$) 12.90 (1H, dr s, CO$_2\underline{H}$), 8.98 (1H, d, J 8.0 Hz), 8.45 (1H, d, J 3.4 Hz), 7.70–7.03 (9H, m), 4.72–4.60 (1H, m, CH), 3.20 (1H, dd, J 14.0, 4.5 Hz, C$\underline{H}_A$H$_B$) and 3.01 (1H, dd, J 14.0, 9.9 Hz, CH$_A\underline{H}_B$); m/z (ESI, 60V) 475 (MH$^+$).

EXAMPLE 10

(N-2-Chloronicotinoyl)-4-[2-(2,6-dichlorophenyl)-2-hydroxyethyl]phenylalanine Lithium hydroxide monohydrate (13 mg) was added to a solution of Intermediate 22 (150 mg, 0.29 mmol) in THF (5 ml) and H$_2$O (5 ml). The solution was stirred for 1 h and then the THF removed in vacuo and the remaining aqueous solution acidified to pH6 with 1M hydrochloric acid. The solid precipitate formed was collected by filtration, washed with copious quantities of water and finally freeze dried to give the title compound as a fluffy white solid (70 mg, 49%). δH (DMSO-$d_6$) 12.78 (1H, br s, CO$_2\underline{H}$), 8.90 (1H, d, J 8.0 Hz), 8.45 (1H, d, J 4.8 Hz), 7.63–7.58 (1H, m, ArH), 7.49–7.45 (1H, m, ArH), 7.34–7.07 (7H, m, ArH), 5.50–5.45 (1H, m, CH), 4.61–4.51 (1H, m, CH) and 3.30–2.35 (4H, m, 2×CH$_2$); m/z (ESI, 60V) 493 (MH$^+$).

EXAMPLE 11

(N-2-Chloronicotinoyl)-{4-[2-(2-dichlorophenyl)-2-oxoethyl]}phenylalanine

Lithium hydroxide monohydrate (36 mg, 0.85 mmol) was added to a solution of Intermediate 23 (400 mg, 0.77 mmol) in THF (5 ml) and water (5 ml). The reaction mixture was stirred for 3 h and then the THF was removed in vacuo. The remaining aqueous solution was acidified with 1M hydrochloric acid. The resulting white precipitate was collected and washed well with water. Further purification by column chromatography (SiO$_2$; acetic acid: MeOH:DCM, 2:8:90) gave the title compound as a white solid (78 mg, 19%). δH (DMSO-$d_6$) 8.45 (1H, dd, J 4.8, 2.0 Hz), 8.03 (1H, dd, J 7.7, 2.0 Hz), 7.36–7.20 (8H, m, ArH), 6.98 (1H, d, J 7.2 Hz, ArH), 5.14–5.05 (1H, m, CH), 4.11 (2H, s, C$\underline{H}_2$C=O)m, 3.39 (1H, dd, J 14.1, 5.6 Hz, C$\underline{H}_A$H$_B$) and 3.25 (1H, dd, J 14.1, 6.2 Hz, CH$_A\underline{H}_B$); m/z (ESI, 60V) 491 (MH$^+$).

α$_4$β$_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigman R4507) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY Cell Adhesion to MAdCAM-Ig

This assay was performed in the same manner as the α$_4$β$_1$ assay except that MAdCAM-Ig (150 ng/ml) was used in place of 2d VCAM-Ig and a sub-line of the β-lympho blastoid cell-line JY was used in place of Jurkat cells.

The IC$_{50}$ value for each test compound was determined as described in the α$_4$β$_1$ integrin assay.

α$_5$β$_1$ Integrin-dependent K562 cell adhesion to fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-dependent human polymorphonuclear neutrophils adhesion to plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 µl in the presence of 10 ng/ml phorbol-12-myristate-13-acetate, and in the presence of absence of test compounds, and incubated for 20 min at 37° C. followed by 30 min. at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% $H_2O_2$ (Sigma) and 50 µg/ml TMB (Boehringer Mannheim) in 0.1M sodium acetate/citrate buffer, pH 6.0 and absorbance measured at 630 nm.

αIIb/β$_3$ -dependent human platelet aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter; NaCl 8.0; $MgCl_2.H_2O$ 0.427; $CaCl_2$; KCl 0.2; D-glucose 1.0; $NaHCO_3$ 1.0; $NaHPO_4.2H_2O$ 0.065). Aggregation was monitored following addition of 2.5 µM ADP (Sigma) in the presence or absence of inhibitors.

In the above assays the compounds of the invention generally have $IC_{50}$ values in the $α_4β_1$ and $α_4β_7$ assays of 1 µM and below. Thus compounds of the Examples typically had $IC_{50}$ values of 100 nM and below in these assays and demonstrated selective inhibition of α4β1. In the other assays featuring α integrins of other subgroups the same compounds had $IC_{50}$ values of 50 µM and above thus demonstrating the potency and selectivity of their action against $α_4$ integrins.

What is claimed is:

1. A compound of formula (1):

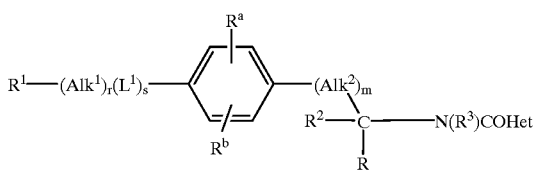

(1)

wherein:

R$^1$ is an optionally substituted $C_6$–$C_{12}$ aromatic group or a $C_1$–$C_9$ heteroaromatic group containing one, two, three, or four heteroatoms selected from oxygen, sulphur or nitrogen;

R$^2$ is a hydrogen atom or methyl group;

R$^3$ and R$^4$, which may be the same or different, is each a hydrogen atom or a straight or branched alkyl group;

R is a carboxylic acid group (—$CO_2H$) or an ester or amide deriviate thereof;

Alk$^1$ is an optionally substituted aliphatic chain;

Alk$^2$ is a straight or branched alkylene chain;

L$^1$ is linker atom or group from —O—, —S—, —C(O)—, —C(O)O—, —C(S)—, —S(O)—, —S(O)$_2$—, —N(R$^4$)—, —OC(O)N(R$^4$)—, —CSN(R$^4$)—, —C(O) N(R$^4$)—, —N(R$^4$)CO—, —N(R$^4$)C(O)O—, —N(R$^4$) CS—, —S(O)N(R$^4$)—, —S(O)$_2$N(R$^4$)—, —N(R$^4$)S (O)—, N(R$^4$)S(O)$_2$—, —N(R$^4$)CON(R$^4$)—, —N(R$^4$) CSN(R$^4$)—, —N(R$^4$)SON(R$^4$)— and —N(R$^4$)SO$_2$N (R$^4$)—;

R$^a$ and R$^b$, which may be the same or different, is each an atom or group —L$^2$(CH$_2$)$_p$L$^3$(R$^c$)$_q$;

L$^2$ and L$^3$ are each covalent bond;

R$^c$ is hydrogen or halogen atom or a group selected from straight or branched alkyl, —OR$^d$, —SR$^d$, —NR$^d$R$^e$, —NO$_2$, —CN, —CO$_2$R$^d$, —SO$_3$H, —SO$_2$R$^d$, —OCO$_2$R$^d$, —CONR$^d$R$^e$, —OCONR$^d$R$^e$, —CSNR$^d$R$^e$, —COR$^d$, —N(R$^d$)COR$^e$, —N(R$^d$)CSR$^e$, —SO$_2$N(R$^d$)(R$^e$), —N(R$^d$)SO$_2$R$^e$, —N(R$^d$)CONR$^e$R$^f$, —N(R$^d$)CSNR$^e$R$^f$ or —N(R$^d$)SO$_2$NR$^e$R$^f$;

R$^d$, R$^e$ and R$^f$, which may be the same or different, is each a hydrogen atom or an optionally substituted straight or branched alkyl group;

p is zero or the integer 1;

q is an integer 1, 2 or 3;

m is zero or an integer 1;

r and s, which may be the same or different, is each zero or an integer 1; and

Het is an optionally substituted $C_{3-5}$ monocyclic heteroaromatic group containing one, two or three heteroatoms selected from oxygen, sulphur or nitrogen atoms;

with the proviso that when L$^1$ is —C(O)N(R$^4$)— and is 1, r is other than 0;

or the salts, solvates, hydrates, or N-oxides thereof.

2. A compound according to claim 1 wherein Het is an optionally substituted pyrrolyl or pyridyl group.

3. A compound according to claim 1 wherein R is a —$CO_2H$ group.

4. A compound according to claim 1 wherein Alk$^2$ is a —$CH_2$— chain and M is an integer 1.

5. A compound according to claim 1 wherein each of R$^2$ and R$^3$ is a hydrogen atom.

6. A compound according to claim 1 wherein —(Alk$^1$)r (L$^1$)s is a —$CH_2O$— group.

7. A compound according to claim 1 which is selected from the group consisting of:

2-Thio(S-2,5-dimethoxyphenyl)nicotinoyl-(N-2,6-dichlorobenzoyl)-L-4-aminophenylalanine;

N-(3,5-Dichloro-4-picolyl)-N'-(3,5-dichloro-4-picolyl)-L-4-aminophenylalanine;

N-(2-Chloronicotinoyl)-N'-(3,5-dichloro-4-picolyl)-L-4-aminophenylalanine;

O-(2,6-dichlorobenzyl)-N-(4-acetyl-1,2,5-trimethyl-3-pyrrolyl)-L-tyrosine;

(N'-3,5-Dichloroisonicotinoyl)-N-{([3-pyridinylmethyl] thio)isonicotinyl}-L-4-aminophenylalanine; and N-(4-Acetyl-1,2,5-trimethyl-1H-pyrrole-3-carbonyl)-N'-3,5-dichloro-4-picolyl)-L-4-aminophenylalanine;

or the salts, solvates, hydrates and N-oxides thereof.

8. A pharmaceutical composition comprising a compound according to claim 1 together with one or more pharmaceutically acceptable carriers, excipients or diluents.

9. A method for the prophylaxis or treatment of a disease or disorder in a mammal in which the extravasation of leukocytes plays a role, comprising administering to a mammal suffering from such a disease or disorder a therapeutically effective amount of a compound according to claim 1.

10. A method according to claim 9 wherein said disease or disorder is selected from the group consisting of inflammatory arthritis, multiple sclerosis, allograft rejection, diabetes, inflammatory dermatoses, asthama and inflammatory bowel disease.

11. A method according to claim 10 wherein said inflammatory arthritis is selected from the group consisting of rheumatoid arthritis vasculitis and polydermatomyositis.

12. A method according to claim 10 wherein said inflammatory dermatoses are selected from the group consisting of psoriasis and dermatitis.

13. A method for inhibiting, in mammal, the binding of α4 integrins to the ligands thereof, comprising administering to the mammal an effective amount of a compound according to claim 1.

14. A method according to claim 13 wherein said α4 integrins are selected from the group consisting of α4β1 and α4β7 integrins.

15. A compound to claim 1 wherein compound of formula (1) has the formula:

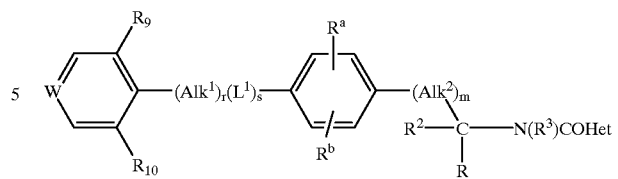

wherein:
—W= is —CH= or —N=; $R^9$ and $R^{10}$, which may be the same or different, is each an atom or group —$L^2$ $(CH_2)_pL^3(R^c)_q$; and r and s are each an integer 1.

16. A compound according to claim 15 wherein $(Alk^1)_r$ $(L^1)_s$ is —$CH_2O$—, $R^2$ and $R^3$ are each a hydrogen atom, $Alk^2$ is —$CH_2$—, and m is 1.

17. A compound according to claim 16 wherein Het is an optionally substituted pyrrolyl or pyridyl group.

18. A compound according to claim 17 wherein R is a —$CO_2H$ group.

19. A compound according to claim 18 wherein $R^a$ and $R^b$ are each a hydrogen atom.

* * * * *